(12) United States Patent
Kelleher et al.

(10) Patent No.: US 8,961,545 B2
(45) Date of Patent: Feb. 24, 2015

(54) SOFT TISSUE ANCHORING METHODS AND DEVICES

(76) Inventors: Brian Kelleher, Del Mar, CA (US); Corbett Stone, Poway, CA (US)

( * ) Notice: Subject to any disclaimer, the term of this patent is extended or adjusted under 35 U.S.C. 154(b) by 2113 days.

(21) Appl. No.: 11/988,751

(22) PCT Filed: Mar. 16, 2005

(86) PCT No.: PCT/US2005/008737
§ 371 (c)(1),
(2), (4) Date: Jan. 14, 2008

(87) PCT Pub. No.: WO2005/089373
PCT Pub. Date: Sep. 29, 2005

(65) Prior Publication Data
US 2011/0098730 A1    Apr. 28, 2011

Related U.S. Application Data

(60) Provisional application No. 60/553,527, filed on May 21, 2004.

(51) Int. Cl.
| | |
|---|---|
| *A61B 17/08* | (2006.01) |
| *A61B 17/122* | (2006.01) |
| *A61B 17/04* | (2006.01) |
| *A61B 17/128* | (2006.01) |
| *A61F 5/00* | (2006.01) |
| *A61B 17/00* | (2006.01) |

(52) U.S. Cl.
CPC ........... *A61B 17/122* (2013.01); *A61B 17/0469* (2013.01); *A61B 17/1227* (2013.01); *A61B 17/1285* (2013.01); *A61F 5/0086* (2013.01); *A61B 17/00234* (2013.01); *A61B 17/0487* (2013.01); *A61B 2017/00004* (2013.01); *A61B 2017/00734* (2013.01); *A61B 2017/00818* (2013.01); *A61B 2017/00827* (2013.01); *A61B 2017/00867* (2013.01); *A61B 2017/0409* (2013.01); *A61B 2017/0464* (2013.01); *A61B 2017/0496* (2013.01)
USPC .......................................... 606/153; 606/213

(58) Field of Classification Search
USPC ......... 606/151, 153, 213, 215, 216, 219, 232; 623/11.11, 23.72
See application file for complete search history.

(56) References Cited

U.S. PATENT DOCUMENTS

| | | | | |
|---|---|---|---|---|
| 5,366,460 | A * | 11/1994 | Eberbach ...................... | 606/151 |
| 6,623,492 | B1 * | 9/2003 | Berube et al. ................. | 606/151 |
| 6,893,452 | B2 * | 5/2005 | Jacobs .......................... | 606/215 |
| 7,160,312 | B2 * | 1/2007 | Saadat .......................... | 606/153 |
| 7,172,615 | B2 * | 2/2007 | Morriss et al. ................ | 606/215 |
| 7,806,905 | B2 * | 10/2010 | Ford et al. .................... | 606/151 |

* cited by examiner

*Primary Examiner* — Julian W Woo
(74) *Attorney, Agent, or Firm* — Merle W. Richman, Esq.

(57) ABSTRACT

Novel devices (120) and methods for soft tissue anchoring and securement are disclosed, such devices and methods offering the advantage of enabling secured tissue to withstand significant forces after such securement is complete. The novel tissue anchoring elements (28) include a force-distributing device that has a large surface area relative to conventional tissue securement devices such as sutures and staples. The force-distributing device (28) may be implanted to a controlled depth into the tissue mass by forming a pocket in a tissue mass and inserting the device, or by slowly driving the device into tissue means of an erosion mechanism such as local pressure necrosis (56). The erosion process may be driven by a force-producing element that may also include a tissue-grasping element (144).

13 Claims, 22 Drawing Sheets

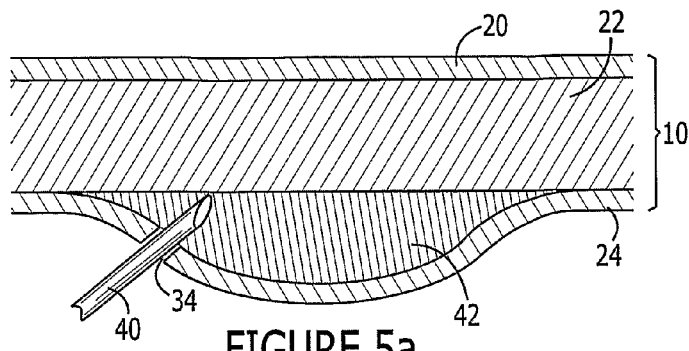
FIGURE 5a
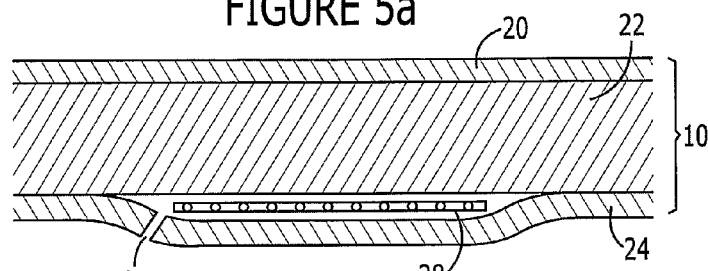
FIGURE 5b
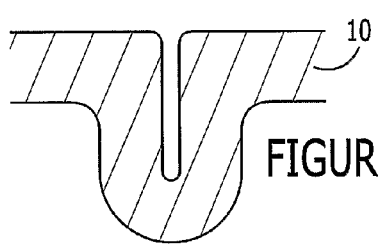
FIGURE 6a
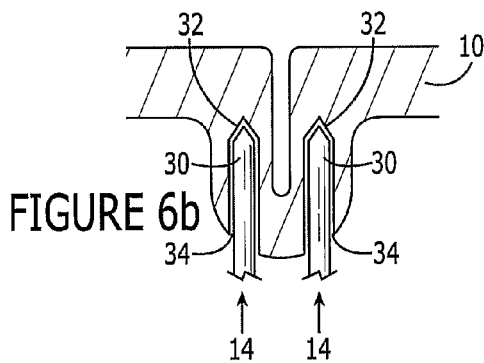
FIGURE 6b
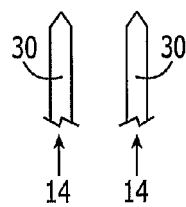
FIGURE 6c

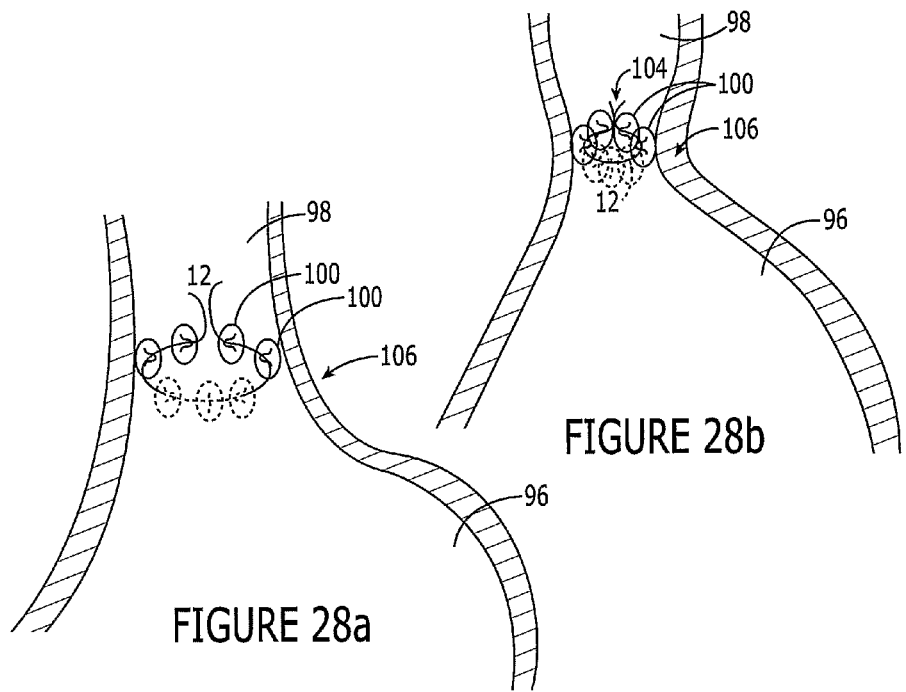
FIGURE 28a
FIGURE 28b
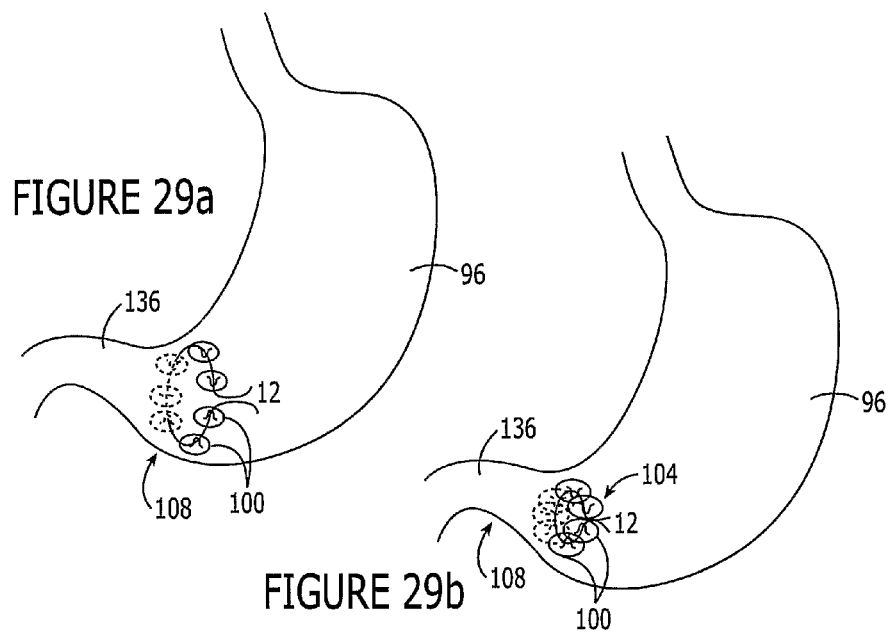
FIGURE 29a
FIGURE 29b

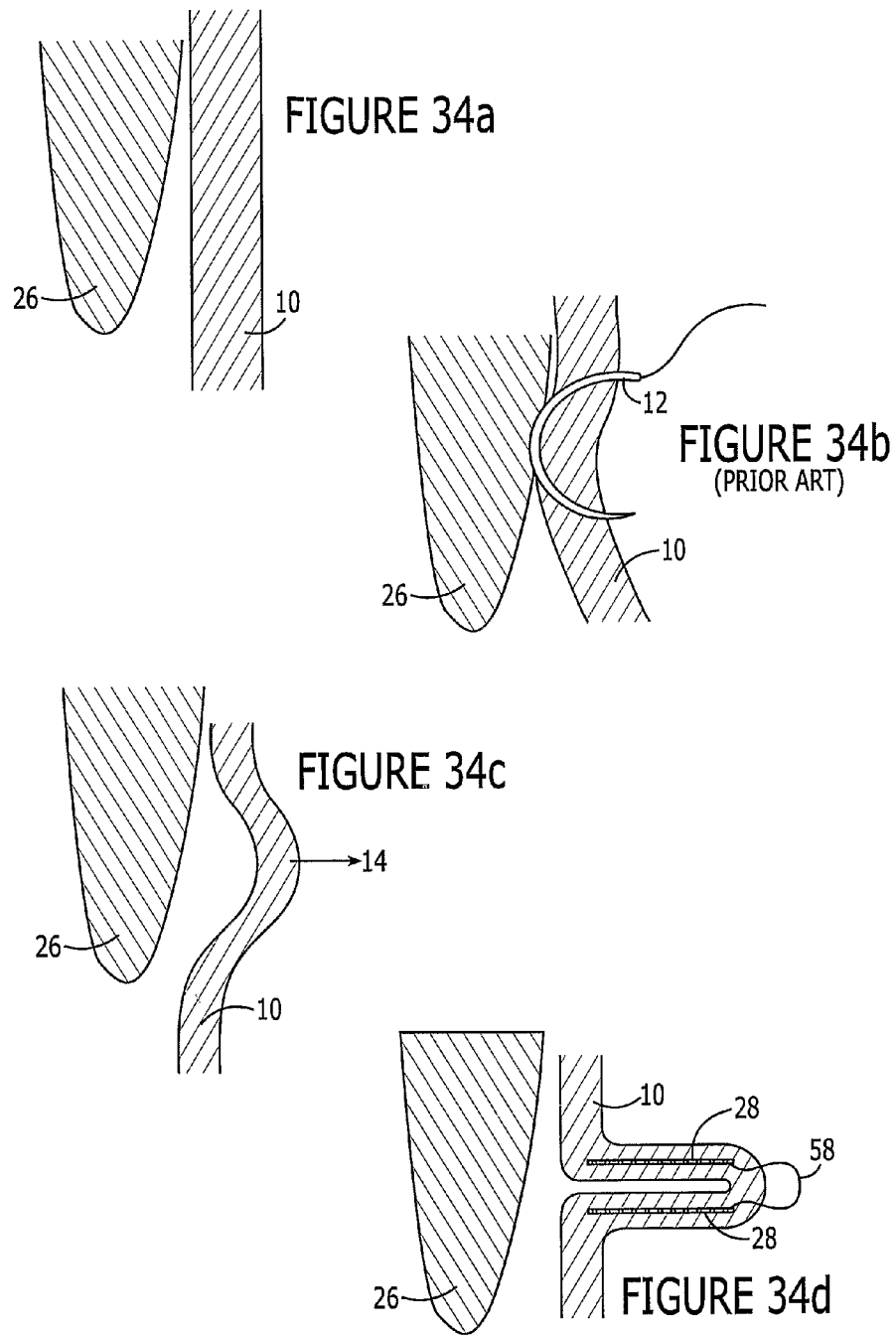

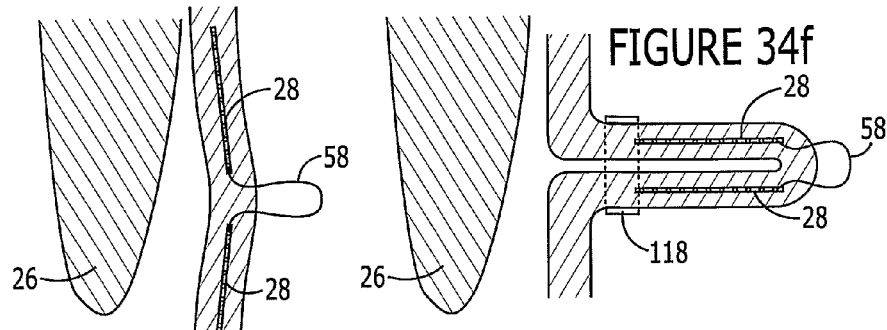
FIGURE 34e
FIGURE 34f
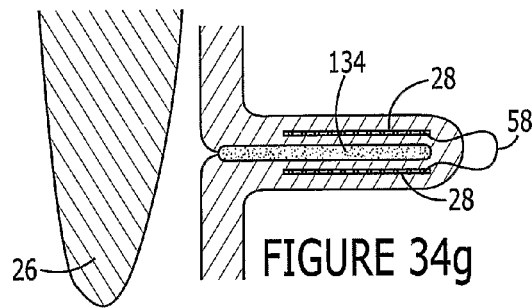
FIGURE 34g
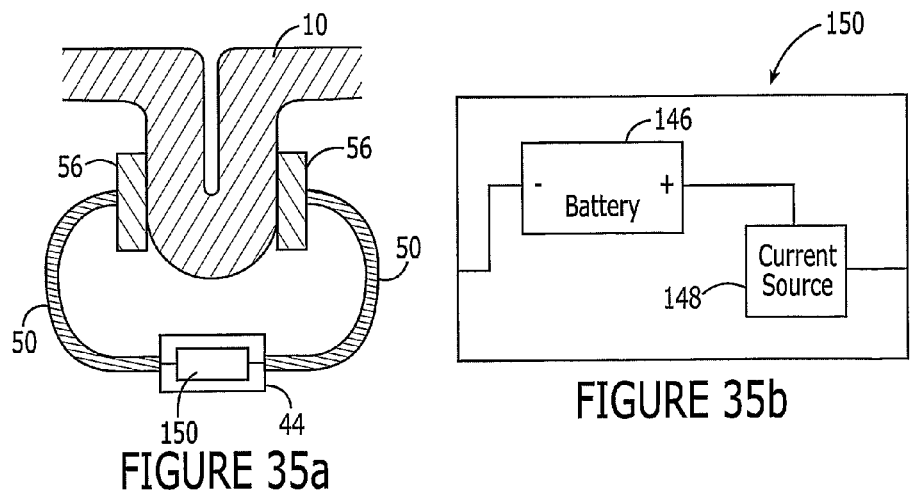
FIGURE 35a
FIGURE 35b

SOFT TISSUE ANCHORING METHODS AND DEVICES

BACKGROUND

1. Field of the Invention

The invention relates to surgical procedures, and, in particular, to the attachment of soft tissue to other tissue or the attachment of objects to soft tissue.

2. Description of the Related Art

The securement of soft tissue segments together has conventionally been done using suturing or stapling devices. However, when attaching segments of soft tissue together that are exposed to tension post-operatively, such techniques often do not hold up over time. This is particularly true for segments of the gastrointestinal (GI) tract. For example, when performing a gastric restriction procedure, such as gastroplasty, simply sewing the anterior and posterior walls of the stomach together often does not hold up over time. Part of the reason for this is that the lining of the stomach does not tend to grow across the sewn seam, as is often the case for other types of tissues and organs when sewn together. Also, with a gastric restriction in particular, the sewn seem is subject to significant stresses post-operatively, when patients try to eat more food than can fit into the reduced stomach compartment created by the sewn seam.

Multiple rows of staples tend to hold up better in these types of applications, not because they grip the tissue better, but because they tend to cause a band of tissue necrosis that induces scarification across the walls of the stomach. Such stomach stapling procedures hold up even better when the stapled tissue is cut along the midline of the multiple rows of staples. Cutting the tissue tends to trigger a wound healing effect that leads to wall-to-wall scarification.

Such multiple-row stapling and cutting of tissue is often neither practical nor desirable, as in the case of flexible endoscopic or endoluminal surgery, where such procedures would be difficult and dangerous. Further, in certain types of elective surgery, such as gastric restriction, it may be desirable to have the procedure be reversible, and reversibility is difficult after tissue has been stapled and cut.

Additionally, when attaching a foreign body to a segment of soft tissue using attachment techniques such as suturing, if the foreign body is subject to forces postoperatively, the foreign body will typically pull loose from the tissue segment.

There is, therefore, a need for robust tissue securement devices and methods which enable tissue-to-tissue attachment and attachment of foreign bodies to tissue with less chance of detachment occurring post-operatively if the securement devices are placed under tension. Moreover, there is a need for robust tissue securement devices which can be delivered endoscopically, as through a rigid endoscope, or endoluminally, as through a flexible endoscope. There is a further need for anchoring devices that enable reversible attachment of tissue-to-tissue and foreign bodies to tissue, and which do so safely with respect to adjacent anatomy.

SUMMARY

The preferred methods, devices and systems described herein provide for improved methods and devices for tissue securement, and, in particular, to soft tissue anchoring elements and their deployment and use.

In a preferred embodiment of the present invention, a tissue securement system comprises a force-distributing device implanted into a tissue mass. The force-distributing device has a large surface area relative to conventional tissue securement devices such as sutures and staples. The force-distributing device is configured to allow conventional tissue securement devices to link to it. In one preferred embodiment, the force-distributing device is comprised of a stand-alone structure embedded within the tissue mass, whereby the securement device, such as a curved-needle suture, is passed into the tissue mass, through the force-distributing device and back out of the tissue mass. In this configuration, forces of tension placed on the suture are distributed not only over the surface area of the portion of the suture within the tissue mass, but also over the surface area of the force-distributing device, assuming an adequate mechanical linkage is obtained between the suture and the force-distributing device. To ensure that such adequate linkage is maintained, in another preferred embodiment, the force-distributing device is configured with an integral linkage element that protrudes from the force-distributing device.

In a preferred embodiment of the invention, the force-distributing device is implanted into the tissue mass by applying a force that causes the force-distributing device to be pushed against the tissue mass. This force is chosen to be great enough to cause the force-distributing device to move gradually into the tissue over time, by means of an erosion mechanism such as local pressure necrosis at the interface between the leading edge of the force-distributing device and the tissue. In preferred embodiments of the invention, the force may be produced by a force-producing element linked to the force-distributing device, such as a spring, expandable material, shape memory element, inflatable element or the like.

In a refinement of certain preferred embodiments, the depth of implantation of the force-distributing device in the tissue is controlled by means such as the use of a force-producing element which provides a force over only a certain range of motion, the use of a force-producing element which degrades after a certain amount of time, or the use of a degradable link between the force-producing element and the force-distributing device which degrades after a certain amount of time.

The depth of implantation may also be controlled by incorporating a stopping surface at a spaced distance from the leading surface of the force-distributing device. The stopping surface has a surface area substantially greater than the area of the leading surface of the force-distributing device. When the force-distributing device moves into the tissue far enough such that the stopping surface comes into contact with the tissue, minimal further movement into the tissue occurs. The force applied by the force-producing element is such that when it is distributed across the surface area of the force-distributing device, a local erosion process occurs, but when it is distributed across the stopping surface, minimal erosion occurs.

The force-distributing device, in combination with the stopping surface, may constitute an implantation assembly that may include other elements. For example, in one preferred embodiment, there is a spacer element between the force-distributing device and the stopping surface. The spacer element preferably has a relatively small surface area so that it does not impede movement of the force-distributing device into the tissue mass. The force-distributing device may be attached to the spacer, or it may be encased in a degradable material that may be part of the spacer and stopping surface structure. In an alternative preferred embodiment, the force-distributing device may be made from a material such as a mesh that can be formed into a shape, such as a pillow, that does not need a spacer element to keep the leading surface at a desired distance from the stopping surface.

In a further refinement of certain preferred embodiments, the force-producing element may include a tissue-grasping element. The tissue-grasping element allows the force-producing element to establish a fixed relationship between the tissue mass and the implantation assembly, so as to exert a force between the two. In a preferred embodiment, the tissue-grasping element consists of an arm that extends at least partially through the tissue mass. In an alternate preferred embodiment, the tissue-grasping element is configured to pinch a segment of tissue and to push at least one implantation assembly into at least one side of the pinched tissue. In a refinement of this embodiment, the system is configured so as to provide enough force to the implantation assembly to move it into the tissue, but not so much force that general ischemia or necrosis of the pinched tissue occurs. The system may also be configured so as to provide enough pinching force so as to encourage knitting of the faces of tissue that are pushed together during the implantation process. For example, in the case where an anchoring system is implanted into the wall of the stomach from the inner lumen of the stomach, it may be desirable to have the outer layer of the stomach wall (serosa) knit together while the tissue is pinched, such that the pinched configuration will remain after the implantation process is complete.

In a particular refinement of the previous preferred embodiments for use in the GI tract, the system may be configured with various degradable linkages such that after the force-distributing device is implanted to the target depth, portions of the system either disintegrate or break into small enough parts, each having smooth features, such that they can be passed through the GI tract without causing harm.

In yet another preferred embodiment, an instrument is described which allows for the endoscopic deployment of one or more anchoring systems under visual guidance.

Various methods relating to the above-described embodiments are also disclosed, including the general method of implanting multiple force-distributing devices into target sites in a tissue mass, lacing the force-distributing devices together with a lacing element such as a thread, and then tightening the thread in order to approximate the sites together. Applications of this method include endoluminal treatment of gastroesophageal reflux disease (GERD) and obesity.

A further refinement of the methods and devices disclosed herein provides for the addition of tissue-affecting substances on or adjacent to the leading or trailing surfaces of the implantation assembly. Such substances may be tissue-dissolving agents, tissue irritants or other substances which facilitate tissue erosion near the leading edge, regrowth of tissue near the trailing edge, and/or fibrotic scarification of tissue around the force-distributing device during or after the implantation process. Additionally, at least a portion of the implantation assembly may be electrically active so as to promote the erosion and/or regrowth and/or fibrotic scarification of tissue during or after implantation of the force-distributing device. Further, at least a portion of the implantation assembly may be activated during or after implantation to induce tissue irritation or scarification by means of thermal injury (either hot or cold). For example, if at least a portion of the force-distributing device is electrically conductive, an electrical current may pass through the force-distributing device and cause a heating effect at the interface between the force-distributing device and the surrounding tissue.

In yet another refinement of certain embodiments, the leading surface of the implantation assembly may be shaped to facilitate erosion. For example, the leading edges of the leading surface of the implantation assembly may be pointed or sharply angled.

BRIEF DESCRIPTION OF DRAWINGS

Having thus summarized the general nature of the invention, certain preferred embodiments and modifications thereof will become apparent to those skilled in the art from the detailed description herein having reference to the figures that follow, of which:

FIG. 2b is a section view of the force-distributing device shown in FIG. 2a.

FIGS. 5a-b are section views showing the placement of a force-distributing device into a pocket created by means of injecting a liquid or gas;

FIGS. 6a-f are section views showing the placement of force-distributing devices into pockets created by use of a pocket-forming tool;

Figure 24:
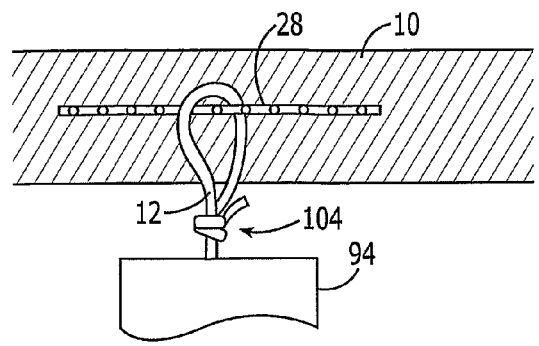
Figure 25A:
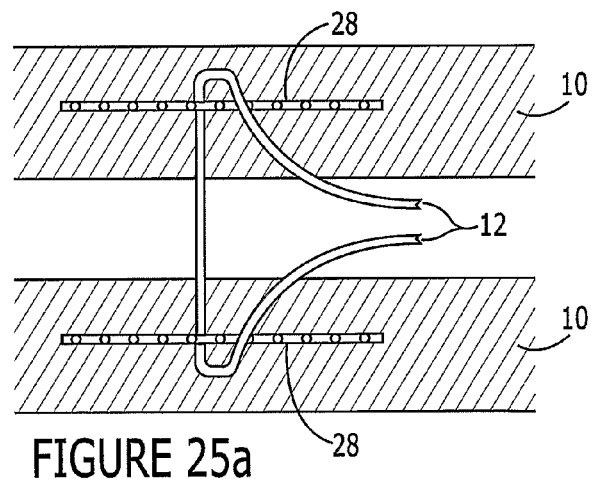
Figure 25B:
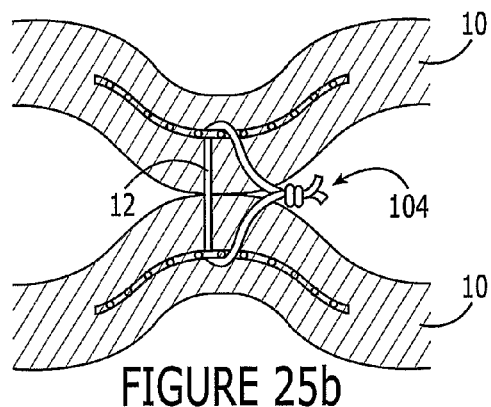
Figure 26:
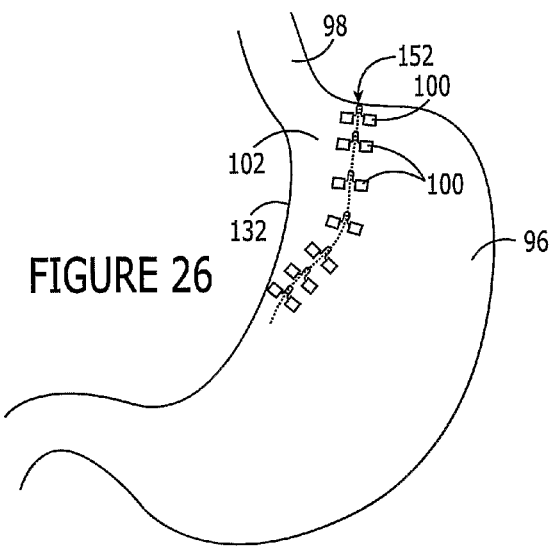
Figure 27A:
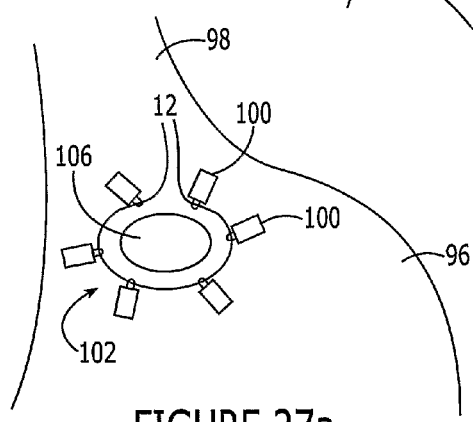
Figure 27B:
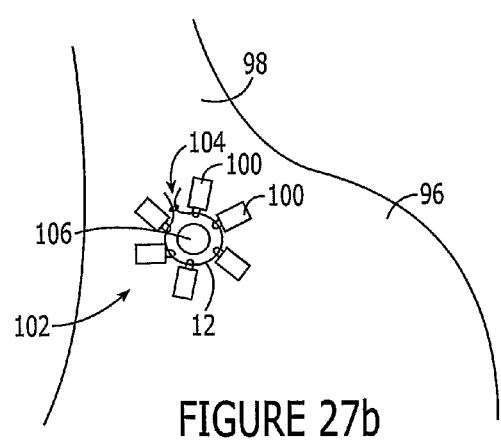
Figure 30:
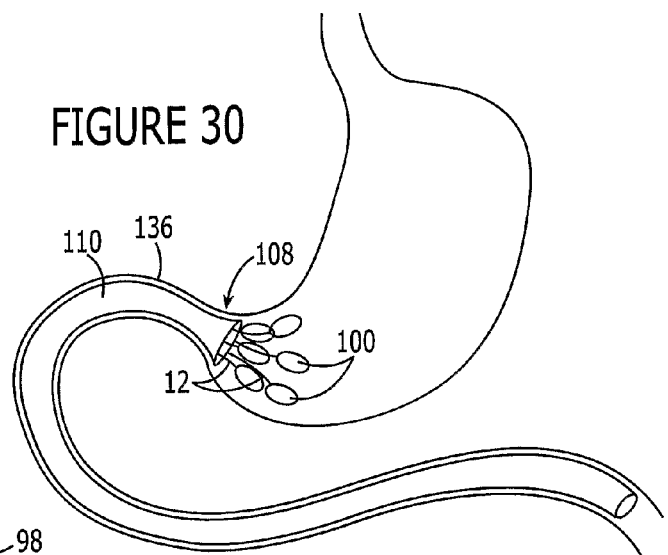
Figure 31:
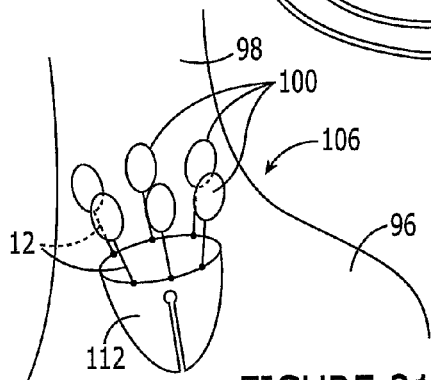
Figure 32:
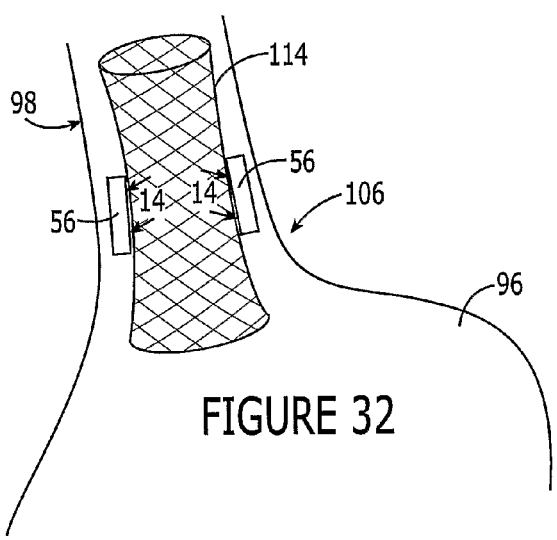
Figure 33A:
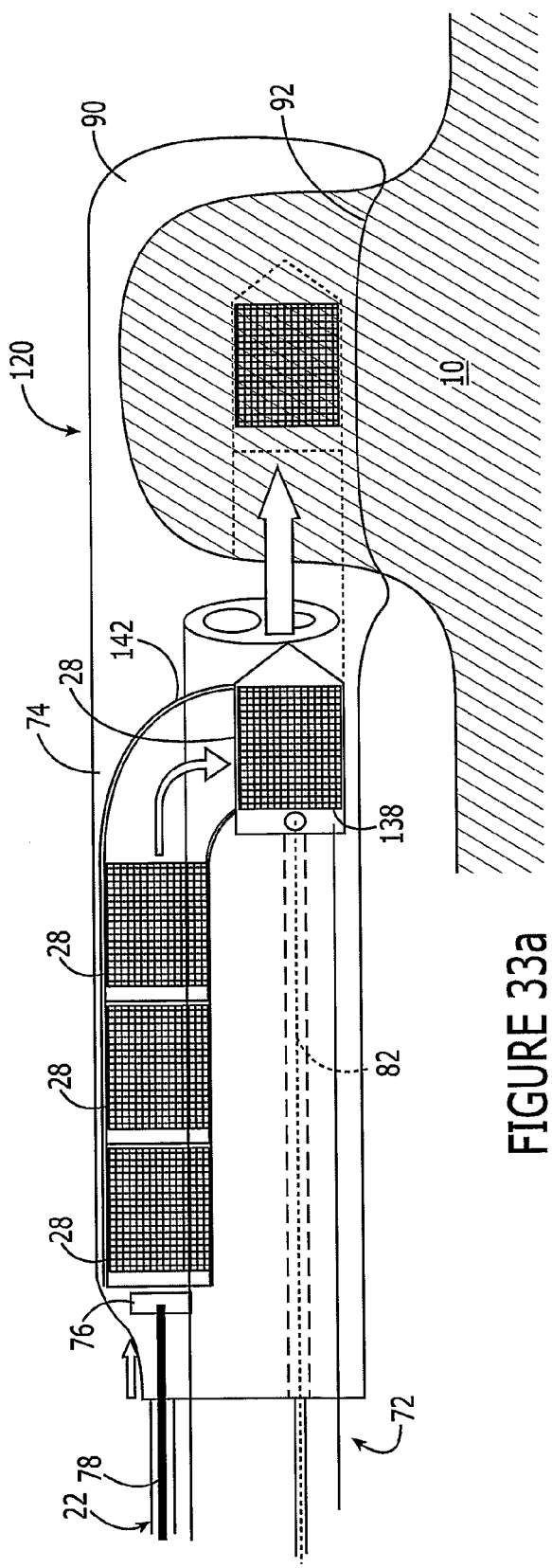
Figure 33C:
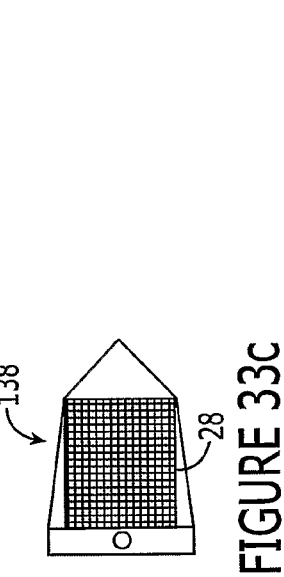
Figure 33B:
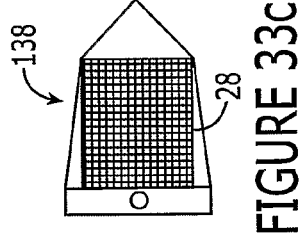

<No FIG. 23>;

FIG. 24 is a section view showing the anchoring system in use for tethering a foreign body to a tissue mass;

FIGS. 25a-b are section views showing multiple tissue masses being approximated by use of multiple force-distributing devices pulled together by a tissue securement device;

FIG. 26 is a schematic view with a cutaway section showing the use of multiple anchoring systems in the stomach to create a gastric restriction for treatment of obesity;

FIGS. 27a-b are perspective views with cutaway sections showing the use of multiple anchoring systems in the cardia region of the stomach to create tightening of the cardia and lower esophageal sphincter for treatment of gastric reflux disease;

FIGS. 28a-b are perspective views with cutaway sections showing the use of multiple anchoring systems in the lower esophageal sphincter region to tighten the sphincter and thereby provide a treatment for gastroesophageal reflux disease;

FIGS. 29a-b are perspective views with cutaway sections showing the use of multiple anchoring systems in the pylorus region of the stomach to constrict the pylorus and thereby provide a treatment for obesity;

FIG. 30 is a perspective view with a cutaway section showing the use of multiple anchoring systems in the pylorus region of the stomach to serve as an anchoring means for a device extending into the duodenum;

FIG. 31 is a perspective view with a cutaway section showing the use of multiple anchoring systems in the lower esophageal region to serve as an anchoring means for a device extending into the stomach;

FIG. 32 is a perspective view with a cutaway section showing the use of a tubular force-producing element such as a stent to press one or more anchoring systems into the wall of the esophagus;

FIG. 33a is a perspective view in partial phantom with certain cutaway views of an endoscopic delivery system that delivers multiple anchoring systems to target tissue masses by means of creating pockets in the tissue and inserting force-distributing devices into the pockets; FIG. 33b is a schematic view of the top edge of the cutting and insertion device shown in FIG. 33a; FIG. 33c is a schematic view of an alternative construction of the cutting and insertion device shown in FIG. 33a;

FIGS. 34a-g are section views showing various tissue securement techniques in relation to surrounding anatomy;

FIG. 35a is a section view of an anchoring system having an electrical current generator; FIG. 35b is a block diagram of the electrical current generator shown in FIG. 35a.

DETAILED DESCRIPTION

The present invention relates to methods and devices for soft tissue securement, and, in particular, to novel anchoring elements and deployment thereof which enable reliable securement of soft tissue to other tissue or to a foreign body.

Figure 1A:
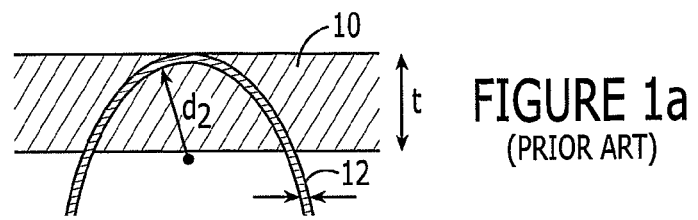
FIGS. 1a-d are section views of prior art tissue securement methods.
Figure 1B:
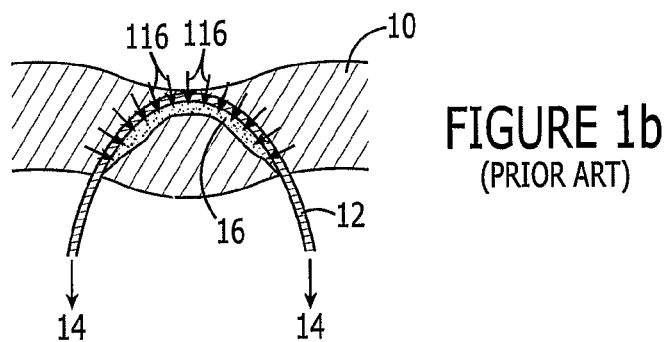
Figure 1C:
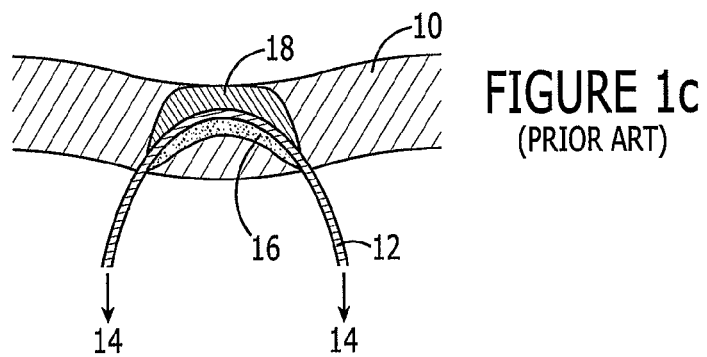
Figure 1D:
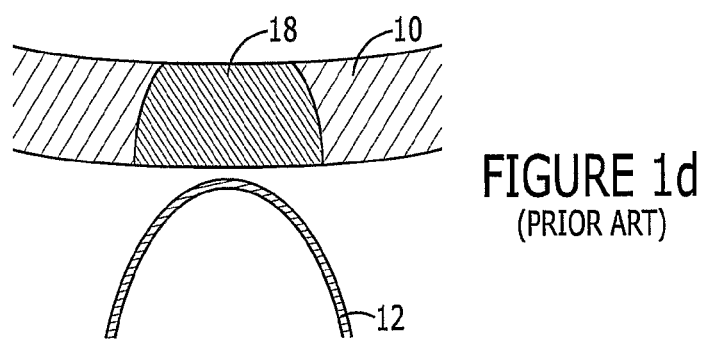

Before describing elements of the present invention, a brief description of prior art devices and methods will be presented. FIG. 1 shows a typical prior art securement device in use with a tissue mass. In FIG. 1a, tissue securement device 12 is shown traversing through tissue mass 10. By way of example, tissue securement device 12 could be a suture placed with a curved needle, or it could be a wire-based anchor such as a staple, helical anchor or shape memory alloy anchor. In FIG. 1b, forces 14 which are exerted on tissue securement device 12 cause compressive forces 116 on the portion of tissue mass 10 indicated as the zone of compression 16. If the resulting pressure exerted by tissue securement device 12 onto zone of compression 16 is sufficient to cause an erosion process, then tissue securement device 12 will move into tissue mass 10, as shown in FIG. 1c. As tissue securement device 12 moves through tissue mass 10, tissue tends to heal around the trailing side of the advancing tissue securement device 12, as indicated in FIG. 1c as zone of regrowth 18. If sufficient forces are applied to tissue securement device 12 over a long enough period of time, tissue securement device 12 can actually move completely through tissue mass 10, as shown in FIG. 1d.

By way of example, referring now to FIG. 1a, if tissue securement device 12 is a fairly thick suture, such as a size 2-0 Prolene (Johnson & Johnson Ethicon Division, Cincinnati, Ohio), the diameter $d_1$ is about 0.013 inches. If the thickness, t, of tissue mass 10 is 0.2 inches (about the thickness of a human stomach wall), and if the arc of the path of tissue securement device 12 through tissue mass 10 has a diameter, $d_2$, of 0.2 inches, then the total surface area of tissue securement device 12 within tissue mass 10 is estimated as: $A=(\pi d_1)*(\pi d_2/2)=(\pi^2*d_1*d_2)/2=0.0128$ in$^2$. If the simplistic assumption is made that all of the compressive forces 116 are distributed evenly along the leading-half surface of tissue securement device 12, then, to a first approximation, the pressure exerted by tissue securement device 12 on tissue mass 10 for a one-pound force is about equal to: force/(half the area of the suture within the tissue)=1 lb/(0.0128 in$^2$)/2=156 pounds/in$^2$ (psi). As will be made clear herein, this pressure is thought to be high enough to lead to an erosion process, allowing tissue securement device 12 to move through tissue mass 10 as shown in FIG. 1d.

Those skilled in the art of surgical stapling believe that a threshold of around 60 psi is enough to induce pressure necrosis, which results when pressure is applied to a tissue mass such that the local blood supply is occluded, leading first to ischemia and then to necrosis. When necrosis of the tissue immediately adjacent to the tissue securement device occurs, the tissue gradually weakens and eventually deteriorates, allowing the securement device to push its way forward into the deteriorating tissue, as long as the securement device continues to have forces acting upon it. This process is thought to provoke a local inflammatory response from the tissue, which is thought to contribute to the process of remodeling tissue around the advancing securement device along its trailing surface. There are likely other factors in addition to pressure necrosis that contribute to the overall erosion process, some of which may involve chemical interaction between the material of the securement device and adjacent tissue, and some of which may involve a relatively slow mechanical interaction (such as abrasion) between the surface of the securement device and adjacent tissue cells, but for purposes of the present invention, the phrase "erosion process" is intended to encompass all of the phenomenon described above.

This erosion process is a particular problem when layers of tissue that are approximated by conventional securement means do not knit together over time. In such cases, the interface between the tissue and the securement devices must bear the long-term stress of keeping the tissue together, whereas with other types of tissue, the tissue knits and relieves the securement device of such stress. As an example, when layers of the stomach are sewn together with conventional suture, the mucosal membranes typically do not knit together. As a result, if the walls of the sewn stomach are subjected to pressures that are translated to tugging forces on the suture which lead to pressure at the interface between the suture and local tissue which exceed the level which triggers the erosion process to occur, the sutures will likely pull through the stomach wall over time. As a result, alternate methods of securing the stomach wall have been developed, such as stapling, wherein a relatively wide band of stomach wall tissue is crushed and held together with multiple rows of staples. The wide band of crushing is thought to cause necrosis and subsequent wall-to-wall healing, a process which is further enhanced when the stomach wall is cut between the rows of staples, which is thought to trigger a more aggressive wound-healing response.

Unfortunately, as discussed in the background section of this disclosure, such multiple-row stapling and cutting of tissue is often neither practical nor desirable, as in the case of flexible endoscopic or endoluminal surgery, where such procedures would be difficult and dangerous. Also, in certain types of elective surgery, such as gastric restriction, it is desirable to have the procedure be reversible, and reversibility is difficult after tissue has been stapled and cut.

An alternative solution is to reduce the forces to which the securement devices will be subjected. One way to do this is to have many more points of securement. However, in the case of endoluminal surgery, it is generally impractical to install more than a few points of securement.

The principal improvement offered by the present invention centers around a better way to address the problem described above, which is to design an anchoring system which distributes tugging forces at each point of securement over a large enough surface area so that even when the maximum anticipated tugging force is encountered, the threshold required to trigger the erosion process will not be reached at the interface between the anchoring device and adjacent tissue. As such, the anchoring device will remain anchored more permanently.

Figure 2A:
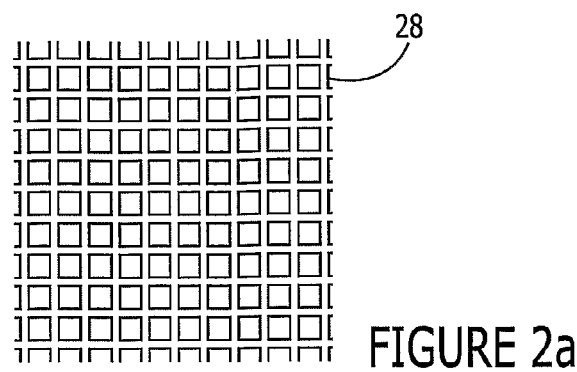
FIG. 2a is a schematic view of a force-distributing device.
Figure 2B:
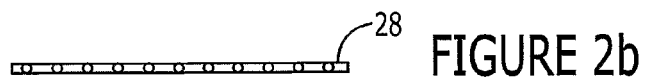
Figure 2C:
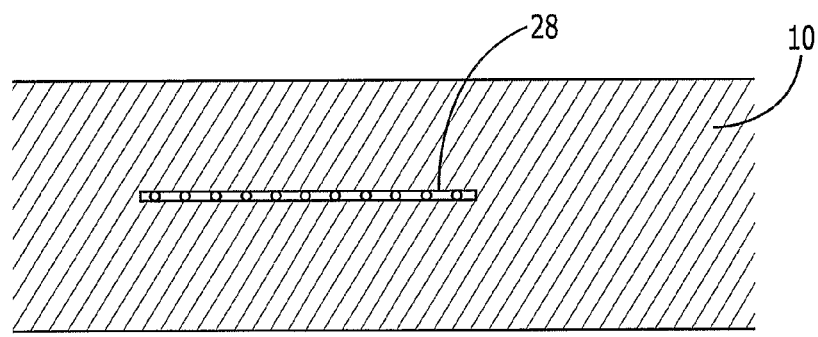
FIG. 2c is a section view showing the force-distributing device of FIG. 2a-b implanted in a tissue mass.

FIG. 2a shows a front view of such an anchoring device, which will be referred to as a force-distributing device 28. FIG. 2b shows an edge view of the same force-distributing device 28 shown in FIG. 2a. The force-distributing device 28 shown may be made from a mesh-type material. It will be understood that the shape and material choice is by way of example only, and is not intended to limit the scope of alternative constructions. FIG. 2c shows force-distributing device 28 implanted in tissue mass 10. It will be appreciated that tissue mass 10 is shown as a single layer, but in practice, it may comprise multiple layers, and force-distributing device 28 may be implanted at a specific target layer to achieve the best anchoring function.

Figure 3A:
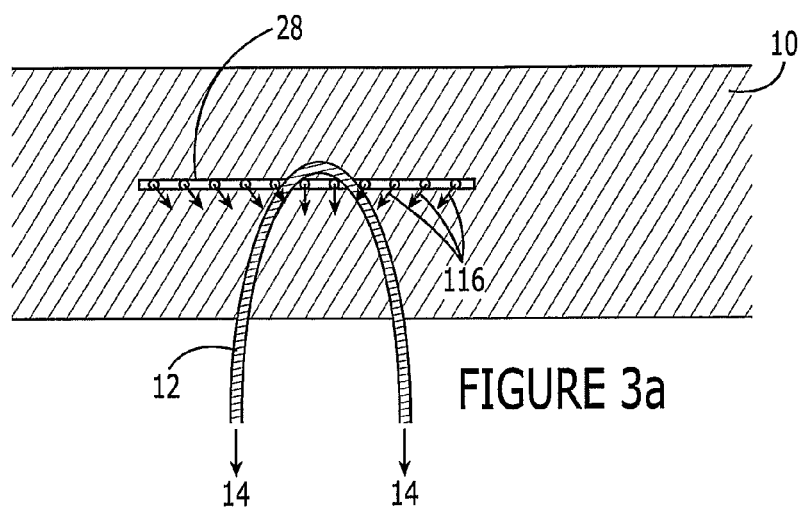
FIGS. 3a-b are section views showing various configurations of the force-distributing device and the way forces exerted upon it externally are redistributed across its surface.
Figure 3B:
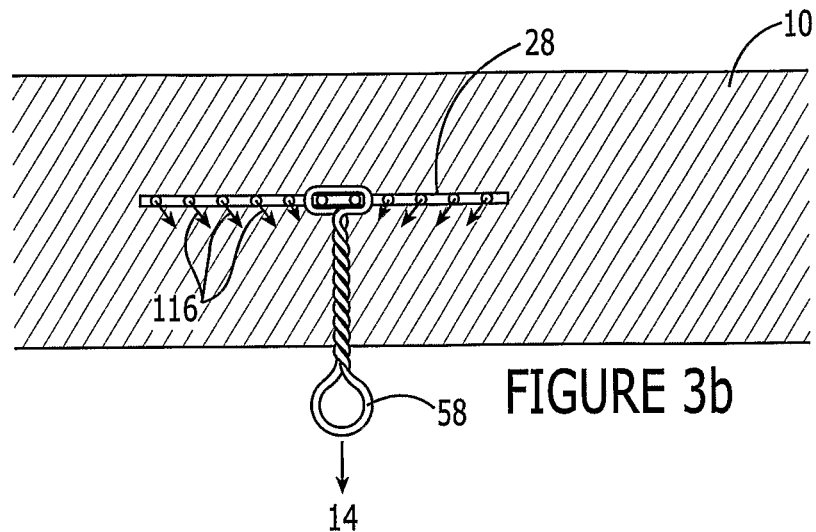

FIG. 3a shows the scenario depicted in FIG. 2c with the addition of tissue securement device 12 that passes through tissue mass 10 and force-distributing device 28, and back out tissue mass 10. By way of example only, tissue securement device 12 may be a suture placed with a curved needle. Forces 14 exerted upon tissue securement device 12 are shown translating to compressive forces 116 between the force-distributing device 28 and local sections of tissue mass 10 adjacent to force-distributing device 28. FIG. 3b shows an alternative preferred embodiment wherein force-distributing device 28 has a linkage element 58 extending from force-distributing device 28, which may or may not extend to the space outside tissue mass 10. Linkage element 58 is configured to receive a securement device such as a thread or suture, or to link directly to a foreign body. It will be appreciated that the intention of the compressive forces 116 shown in FIGS. 3a and 3b is not to show a quantitative force distribution, but instead to depict qualitatively that the benefit of force-distributing device 28 is to translate a large force 14 into an array of relatively small compressive forces 116, each of which, when translated into a pressure over the interface with adjacent tissue, is below the threshold required to trigger the erosion process.

By way of example, if the diameter of the mesh fibers in force-distributing device 28 are 0.003 inches, and if the fibers are spaced every 0.01 inches, and if the mesh is 0.5 inches square, then there are 100 total fibers in the mesh, and the total surface area of the embedded mesh is: $A=100*(\pi*0.003*0.5) =0.47$ in$^2$. If the simplistic assumption is again made that compressive forces 116 are distributed over the leading half surface of the mesh (in the direction of the tugging force), then the pressure exerted by a one-pound tension force on either the securement device 12 or linkage element 58 translate across the force-distributing device 28 to a pressure on adjacent tissue of approximately: 1 lb/(0.47 in$^2$)/2=2 psi. This pressure is dramatically lower than that shown for the suture example previously, and is thought to be well below the threshold needed to trigger an erosion process.

Figure 4A:
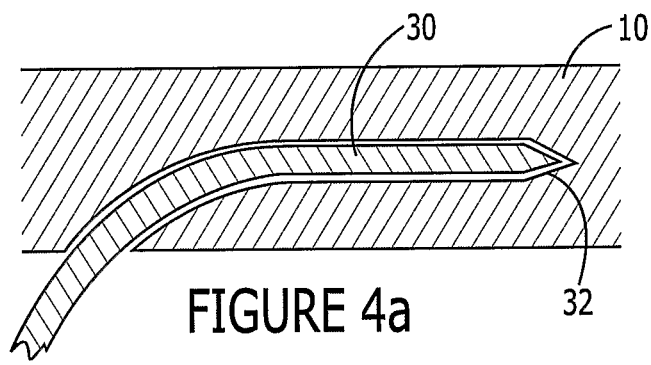
FIGS. 4a-b are section views showing the formation of a pocket in a tissue mass and the insertion of a force-distributing device into the pocket.
Figure 4B:
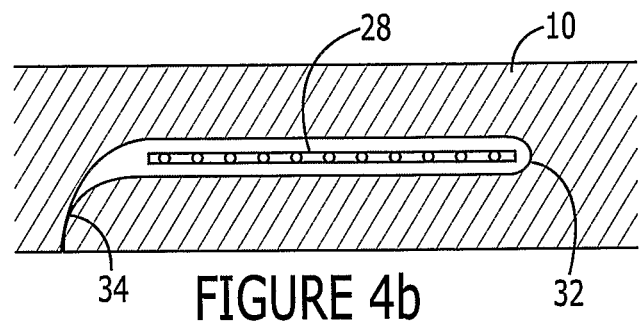

FIGS. 4a and 4b show one technique for implanting force-distributing device 28 into tissue mass 10. In FIG. 4a, a pocket-forming tool 30 is inserted into tissue mass 10 to create a pocket 32. In FIG. 4b, force-distributing device 28 is inserted into pocket 32. Entry wound 34 may be allowed to heal on its own, or it may be glued, stitched, clipped or otherwise secured using techniques familiar to those skilled in the art. Following implantation of force-distributing device into pocket 32, it is desirable that tissue ingrowth occurs from tissue mass 10 into force-distributing device 28 in order to form a strong bond between the two.

FIGS. 5a and 5b show another technique for implanting force-distributing device 28 into tissue mass 10. In this approach, tissue mass 10 is shown having multiple layers—an inner layer 24, an outer layer 20 and a set of intermediate layers 22. FIG. 5a shows needle 40 whose tip is between the inner layer 24 and intermediate layer 22, and shows that a gas or liquid 42 has been injected in order to create a bolus which atraumatically separates the layers. It will be appreciated that instead of using a needle and injecting a substance, this type of blunt dissection may be done using a blunt dissecting tool, an inflatable dissecting balloon or the like. FIG. 5b shows force-distributing device 28 implanted through entry wound 34 into the dissected space.

Figure 6D:
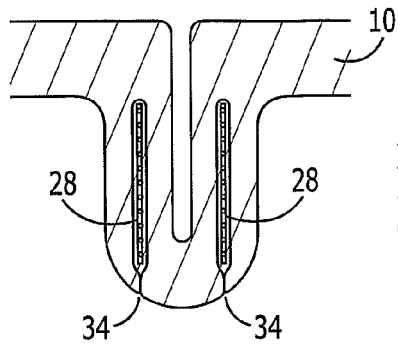
Figure 6E:
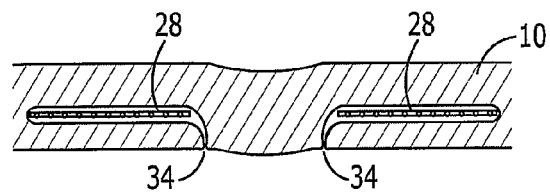
Figure 6F:
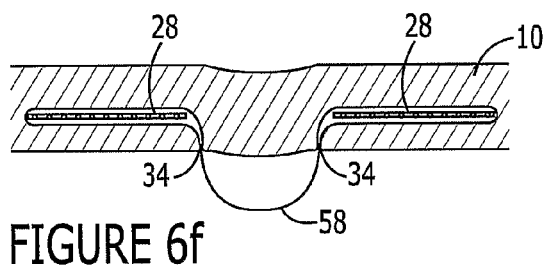

FIGS. 6a-f show another way of implanting force-distributing device 28, wherein tissue mass 10 is first formed into a shape such as a tuck, fold, nipple, pucker, pinch or the like, as shown in FIG. 6a. Next, as shown in FIG. 6b, a dual version of pocket-forming tool 30 is inserted into tissue mass 10 to create a pair of pockets 32. Then, as shown in FIGS. 6c and 6d, a pair of force-distributing devices 28 is inserted into pockets 32. It will be appreciated that instead of a pair of individual pocket-forming tools 32, a single cylindrical tool may be used to implant a force-distributing device 28 which may be cylindrical or ring-shaped. FIG. 6e shows the tissue of FIG. 6d after the force-distributing devices have been implanted and after the tissue has been released and allowed to heal, and preferably grow into the implants. FIG. 6f shows the same outcome from the sequence shown in FIGS. 6a-f, with the change being that instead of independent force-distributing devices, a linked dual force-distributing device is implanted (see FIG. 16e, for example). It will be understood that pocket-forming tool 30 may be adapted to deliver the force-distributing device 28 at the time the pocket is formed. An example of such a tool is described in the embodiment shown in FIG. 33*a-b*, wherein the force-distributing device is carried into the tissue on the side of the tool. Other configurations will be apparent to those skilled in the art, such as tools that deliver force-distributing devices that are deployed from within a lumen in the tool.

Figure 7A:
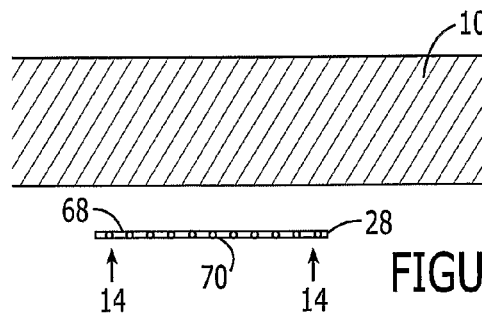
FIGS. 7a-e are section views showing the implantation of a force-distributing device into a tissue mass by means of a force-driven erosion process.
Figure 7B:
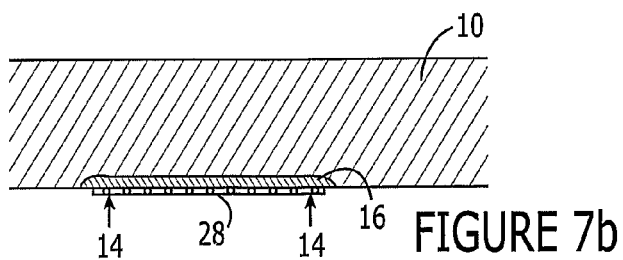
Figure 7C:
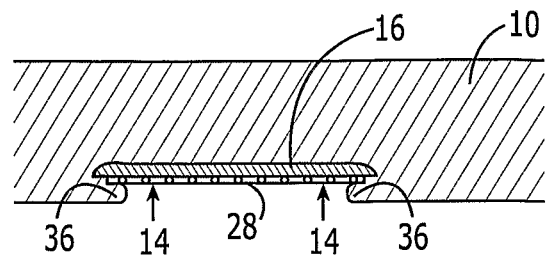
Figure 7D:
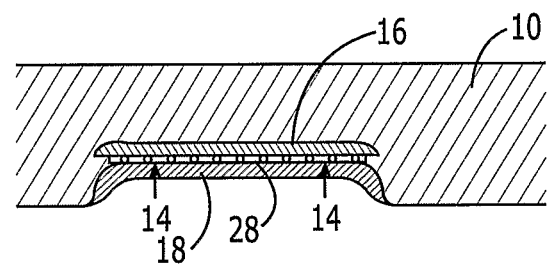
Figure 7E:
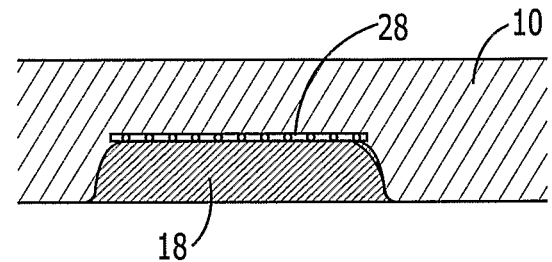

FIGS. 7*a-e* show the basic sequence involved in implanting force-distributing device 28 into tissue mass 10 by taking advantage of the erosion process described previously. In FIG. 7*a*, leading surface 68 of force-distributing device 28 is shown adjacent to a surface of tissue mass 10. Force 14 presses leading surface 68 into tissue mass 10, causing zone of compression 16, shown in FIG. 7*b*. Assuming pushing force 14 is sufficient such that the pressure applied along leading surface 68 at the zone of compression 16 exceeds that required to trigger the erosion process, force-distributing device 28 gradually moves into tissue mass 10. In many cases, tissue mass 10 reacts to the erosion process by triggering an inflammatory response, which helps to trigger remodeling mechanisms such as shown in FIG. 7*c* by the zones of tissue overgrowth 36 which may form around the trailing surface 70. As the process continues, force-distributing device 28 moves more deeply into tissue mass 10, and a zone of tissue regrowth 18 may form along the path, as shown in FIGS. 7*d* and 7*e*. In a preferred embodiment, force-distributing device 28 has a mesh-like structure with an opening size that accommodates tissue ingrowth. There is a desire to have the mesh have as much surface area as possibly to distribute the forces and therefore the pressure as much as possible, but there is also the need to keep the opening size large enough for adequate ingrowth. The optimum opening size will ultimately depend upon the particular tissue type being targeted, and the forces to which the mesh will be subjected. By way of example only, and not by limitation, the opening size of the mesh may be in the range of 100 to 1500 microns, and the mesh fibers may be in the range of 0.0005 to 0.020 inches thick.

Figure 8:
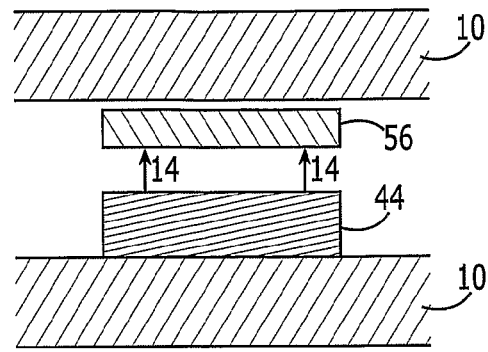
FIG. 8 is a section view showing the anchoring system with the force-producing element exerting a force against the force-distributing device relative to a second tissue mass.

Attention will now be directed toward specific preferred embodiments of anchoring systems that use the erosion process to implant force-distributing devices into tissue. FIG. 8 shows an anchoring system with a force-producing element 44 that exerts a force against implantation assembly 56 (which includes a force-distributing device), whereby implantation assembly 56 is pressed into a first tissue mass 10, by pushing off of a second tissue mass 10.

Figure 9:
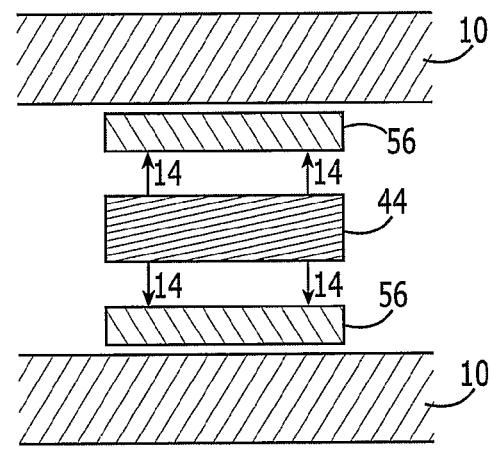
FIG. 9 is a section view showing the anchoring system with the force-producing element exerting a force against multiple force-distributing devices pressed against multiple tissue masses.

FIG. 9 shows an anchoring system with a single force-producing element 44 exerting a force against multiple implantation assemblies 56, which may be pressed against multiple tissue masses 10.

Figure 10:
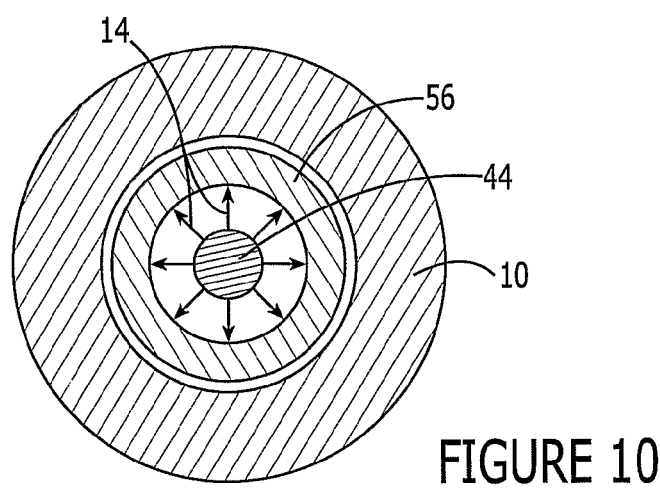
FIG. 10 is a section view showing the anchoring system with a force-producing element exerting a radial force against a circumferential force-distributing device which is being pressed into a surrounding tissue mass.

FIG. 10 shows an anchoring system with a force-producing element 44 exerting a radial force that presses a circumferential implantation assembly 56 into a surrounding tissue mass 10. This embodiment may be used in a tubular organ such as the esophagus, bowel, urethra or vessel, and force-producing element 44 may be constructed of a spring, expanding material, shape memory element, balloon or the like.

Figure 11:
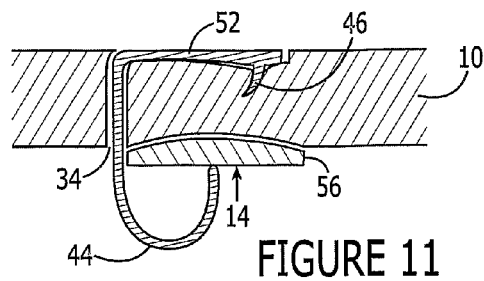
FIG. 11 is a section view of an anchoring system having a tissue-grasping element which extends through the tissue mass.
Figure 12:
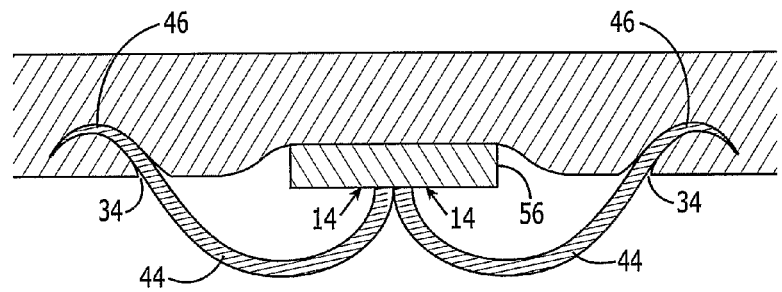
FIG. 12 is a section view of an anchoring system having multiple tissue-grasping elements which are anchored at least part-way in the tissue mass.

FIG. 11 shows an anchoring system having a tissue-grasping element 52 whose purpose is to grasp a segment of tissue mass 10 and hold it in place so that implantation assembly 56 can be pressed into the grasped tissue. In the embodiment shown, force 14 is provided by force-producing element 44, which is shown as being a shaped spring element which functions as both a tissue-grasping element 52 and a force-producing element 44. In FIG. 11, tissue-grasping element 52 is shown extending through tissue mass 10, however that need not be the case, as shown in FIG. 12, wherein an array of tissue-grasping elements are anchored part-way into tissue mass 10, and which also provide the force-producing element 44 function. It should be noted that the portion of each tissue-grasping element anchored in tissue mass 10 preferably has a grip element 46 with a high surface area relative to the direction of exerted force, so that grip elements 46 do not erode through tissue mass 10 themselves.

Figure 13:
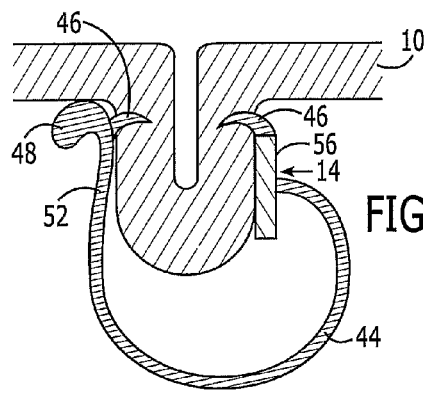
FIG. 13 is a section view showing an anchoring system which presses a single force-distributing device into one side of a pinched portion of a tissue mass.

FIG. 13 shows an anchoring system that presses a single implantation assembly 56 into one side of a pinched portion of tissue mass 10. As with the embodiment shown in FIG. 11, this embodiment has a single formed spring element that serves as both a tissue-grasping element 52 and a force-producing element 44. To keep the tissue from slipping out while the implantation process takes place, tissue-grasping element 52 and implantation assembly 56 preferably each have a grip element 46. It will be appreciated that grip element 46 needs to have sufficiently high surface area so that it will not erode into or out of the tissue. An important design challenge for embodiments that require portions of tissue to be held in a desired shape, such as a tuck, is that the clamping pressure to hold the tissue in the desired shape should not be so excessive as to cause general ischemia and necrosis in the tuck itself. To that end, not only should the clamping pressure be kept to a minimum, but also the surface area of the clamp and/or pattern of clamping across the tuck should be chosen so as not to cause general ischemia. As will be shown in FIGS. 15*d* and 15*f*, a preferred design that addresses this requirement is one in which the clamping force is only applied across a portion of the cross-sectional area of the tuck.

Figure 14:
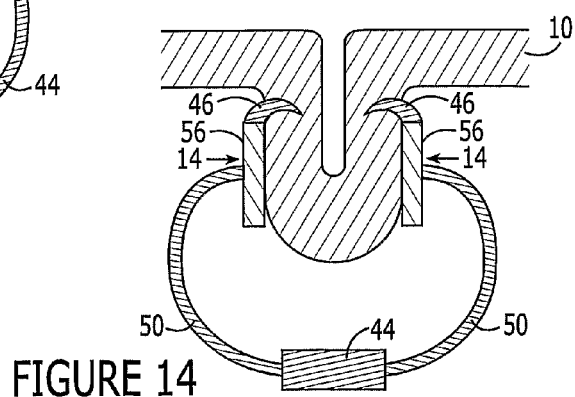
FIG. 14 is a section view showing a dual anchoring system which presses one force-distributing device into each side of a pinched portion of a tissue mass.

The embodiment shown in FIG. 14 is similar to the embodiment shown in FIG. 13, with the addition of a second implantation assembly 56 on the opposite side of the tissue tuck. In this embodiment, both implantation assemblies 56 have grip elements 46 to stabilize the tuck. In the embodiment shown, a force-producing element 44 is disposed above the tuck and a pair of force-translating elements 50 links the force-producing element 44 to each of the implantation assemblies 56. It will be appreciated that the combined function of force-producing element 44 and force-translating elements 50 may be accomplished by a simple curved spring element, as illustrated by the embodiments shown in FIGS. 15*a-g*.

Figure 15A:
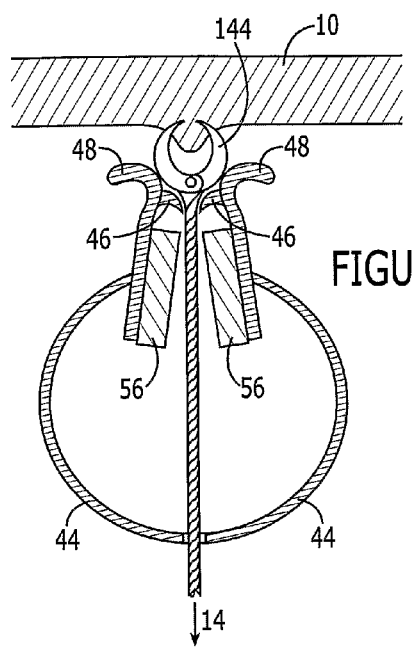
FIGS. 15a-g are section and schematic views showing various configurations of dual anchoring systems.
Figure 15B:
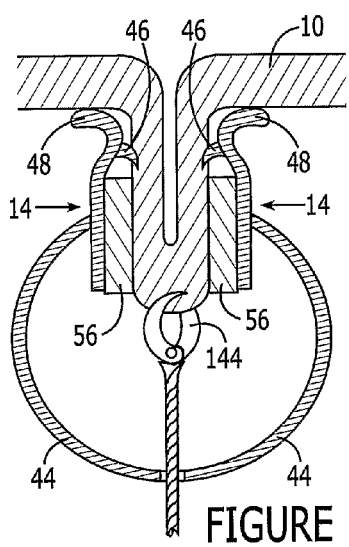
Figure 15C:
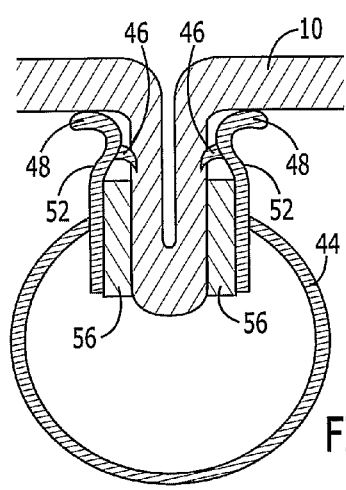
Figure 15D:
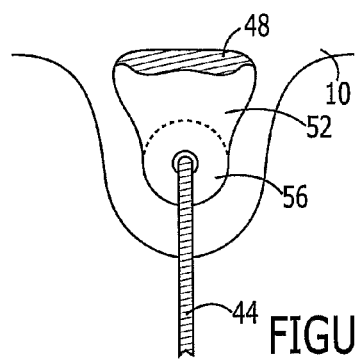

The embodiments shown in FIGS. 15*a-g* are similar to that of FIG. 14, with the simplification described above and the addition of a pair of feet 48, one on each side of the anchoring system. Feet 48 preferably have smooth curved surfaces and are relatively wide such that minimal tissue ischemia, necrosis, erosion or trauma occurs at the base of the pinched tissue tuck. FIGS. 15*a-b* show a technique for grasping a target location on tissue mass 10 and drawing it into the anchoring system. In FIG. 15*a*, tissue grabber 144, which may be a pinching forceps device similar to that shown, or it may be a barb, hook, clip, claw, suction device or the like, is shown grasping the target area of tissue mass 10. In the embodiment shown, tissue grabber 144 is depicted as a separate device that moves through or around the anchoring system. However, it will be appreciated that the function of tissue grabber 144 may be incorporated into the anchoring assembly itself. As shown in FIG. 15*b*, tissue mass 10 is pulled into the anchoring system by tissue grabber 144. The shape of feet 48 may help to guide the tissue into the anchoring system, and the shape of grip elements 46 may assist in keeping the tissue from slipping out as the tissue is drawn inside. In the embodiment depicted in FIGS. 15*c-d*, feet 48 may be linked to either force-producing element 44 or to implantation assemblies 56.

Figure 15E:
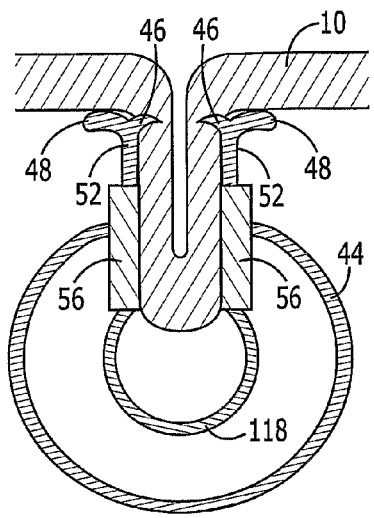
Figure 15F:
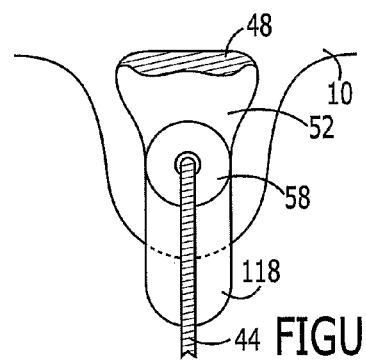

In the embodiment shown in FIGS. 15*e-f*, the force required to keep the tissue pinched is generated separately from the force needed to push implantation assembly 56 into the tissue. As shown, a pinching clamp 118 is linked to tissue-grasping elements 52 and feet 48, while force-producing element 44 separately pushes against implantation assembly 56. Note that in FIGS. 15*d* and 15*f*, the surface area of the combined surfaces of feet 48 and grip elements 46 does not constitute the entire surface area of the tissue tuck, nor do they cut completely across any portion of the tuck, thereby reducing the chance of inducing ischemia in the tuck itself.

Figure 15G:
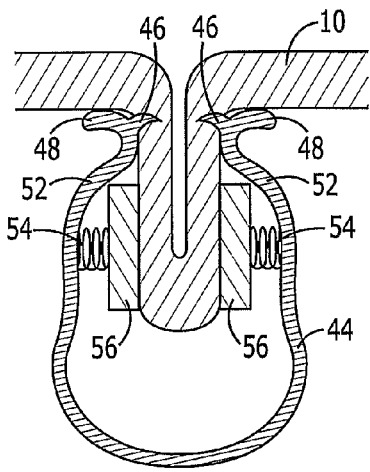
Figure 19:
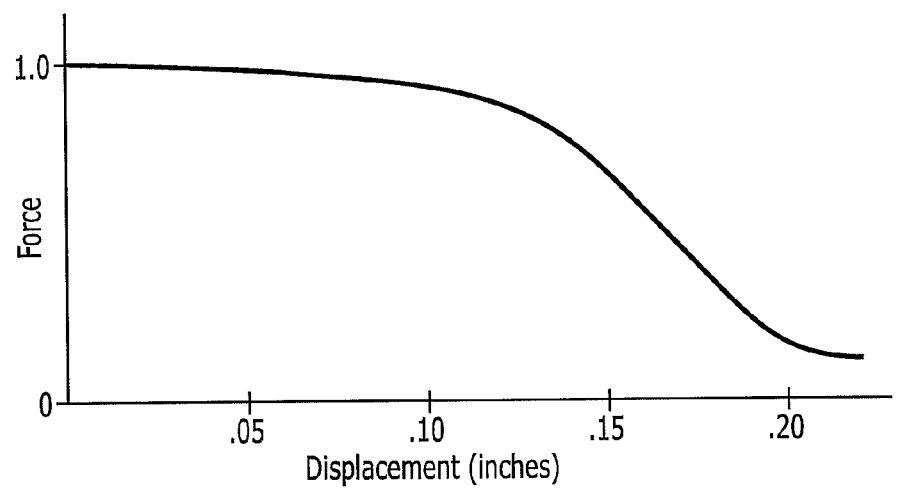
FIG. 19 is a graph showing a force versus displacement curve for a particular force-producing element.

In order to keep the pressure exerted by the leading surface of implantation assembly 56 against the tissue high enough to promote erosion, but yet low enough so as not to cause general tissue ischemia, it may be preferable for force-producing element 44 to exert a relatively constant force on implantation assembly 56. However, assuming force-producing element 44 is a simple spring element, as implantation assembly 56 moves into the tuck, the force exerted by force-producing element 44 will decrease as implantation assembly 56 moves into the tissue. To address this, FIG. 15*g* shows a further refinement of the embodiments shown in FIGS. 15*c-f*, wherein constant force elements 54 are shown positioned between force-producing element 44 and implantation assemblies 56. The design of constant force elements is well known to those skilled in the art. In this configuration, force-producing element 44 is linked directly to tissue grasping elements 52 and feet 48 and provides enough direct force to keep the tissue in its pinched state during the implantation process. Constant force elements 54 are also linked to force-producing element 44 and keep the force applied to implantation assemblies 56 relatively constant, despite fluctuations in the forces applied by force-producing element 44 caused by variations in the thickness of the wall of the tissue being pinched, the size and shape of the tuck itself, as well as variations in force caused by the movement of implantation assembly 56 into the tissue. Alternatively, force-producing element 44 itself may be designed to provide a more constant force over the range of displacement anticipated during the implantation process. By way of qualitative example only, FIG. 19 shows a graph of spring force versus displacement for such a spring element.

The interface between force-producing element 44 and implantation assembly 56 may be a direct, fixed linkage, or it may be a movable linkage. A fixed linkage has the advantage of being simple, and may be designed such that the face or faces of implantation assembly 56 are held relatively parallel to the face of the tissue against which it being pressed. The disadvantage is that variations in tissue thickness and the movement of implantation assembly 56 into the tissue may cause the face or faces of implantation assembly 56 to not be parallel to the tissue, resulting in an asymmetrical distribution of force over the surface of implantation assembly 56 at the tissue interface. A movable linkage design may be accomplished by use of a ball-and-socket linkage between force-producing element 44 and implantation assembly 56, such that as the variations described above are encountered, forces exerted on implantation assembly 56 by force-producing element 44 will be distributed relatively evenly over the leading surface of implantation assembly 56.

Figure 16A:
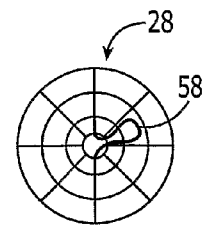
FIGS. 16a-h are perspective views of various configurations of the force-distributing device.
Figure 16B:
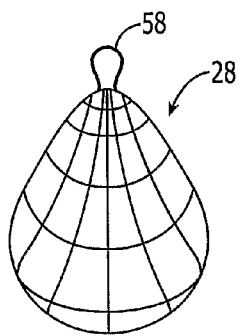
Figure 16C:
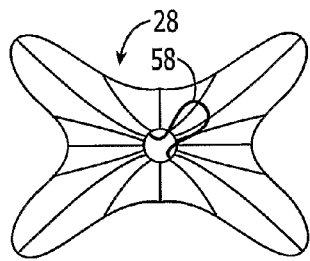
Figure 16D:
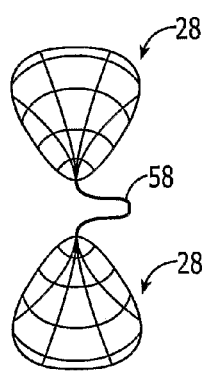
Figure 16E:
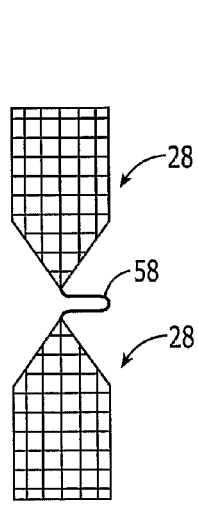
Figure 16F:
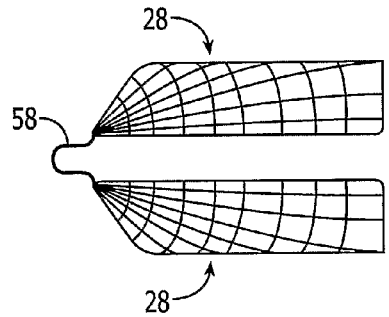
Figure 16G:
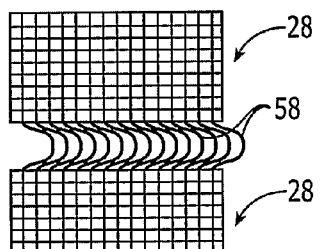
Figure 16H:
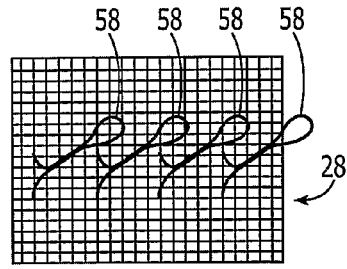

FIGS. 16*a-h* show various configurations of force-distributing device 28. Each configuration is shown with at least one optional linkage element 58 that may extend outside the tissue mass for linkage to a securement device. It will be appreciated that in FIGS. 16*a-h*, the force-distributing devices 28 are represented as mesh-based structures, and only a few representative fibers are shown to depict each general configuration. The actual devices may have different materials and constructions, different proportions of fibers, or the fibers may be arranged in different orientations in order to optimize the distribution of force over the surface area. Further, the cross-sectional shape of the fibers may be other than round. For example, if the cross section was more elliptical, with the long axis aligned with the direction of the driving force during implantation, the mesh would move more easily into the tissue, and would also provide more surface area after implantation for side loads applied to the mesh. FIG. 16*a* shows a substantially circular design with radial spokes and concentric rings. FIG. 16*b* is more triangular in shape, and FIG. 16*c* is shaped like a four-pointed star. Each of the configurations shown in FIGS. 16*a-c* are depicted as single elements, which may be implanted with a single-sided anchoring system, such as the ones shown in FIGS. 11-13, or may be implanted in pairs using a double-sided system such as those shown in FIGS. 14 and 15. In the latter case, the result would be a pair of implanted force-distributing devices 28, each potentially with its own linkage element 58. In a variant of this approach, FIGS. 16*d-g* show paired and linked force-distributing devices 28, wherein linkage element 58 links two separate force-distributing devices 28, which may be implanted using a double-sided anchoring system. FIG. 16*f* may be more appropriate for applications where the tension is applied to linkage element 58 as more of a side or shear load, rather than a load applied primarily orthogonally to the tissue plane, since the load applied to linkage element 58 is distributed over the longer length of force-distributing devices 28. FIGS. 16*g* and 16*h* show alternative forms of force-distributing devices 28 having multiple linkage elements 58. The benefit of multiple linkage elements 58 is that a common load applied to one or more securement devices that are linked to the multiple linkage elements 58 will be more evenly distributed over the surface of the force-distributing devices 28. In all of the above configurations, the design intent is to distribute over the relatively large surface area of force-distributing device 28 a force exerted either through linkage element 58 or through an external securement device such as a suture or staple that is linked to force-distributing device 28. It will be appreciated that there are many additional configurations that will be apparent to those skilled in the art. It will be noted that it is beneficial for the edges of the force-distributing device to be smooth so as not to irritate surrounding tissue after implantation. Such smoothing may be done with chemical, thermal, or mechanical means, or the edges may be coated with a smooth material.

Figure 17A:
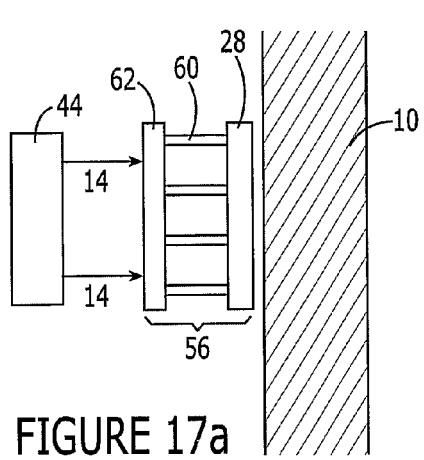
FIGS. 17a-b are section views showing aspects of the anchoring system as it is implanted into a tissue mass.
Figure 17B:
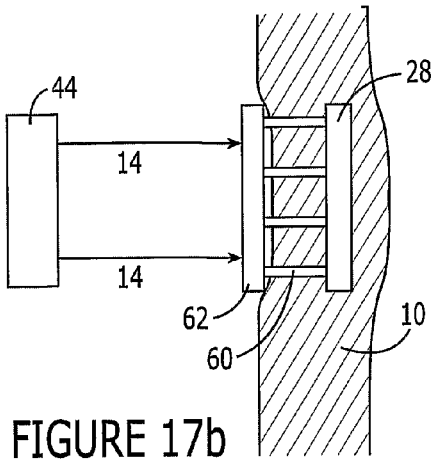

FIGS. 17*a-b* show additional details of a preferred embodiment of the anchoring system. A force-producing element 44 exerts a force 14 onto implantation assembly 56, which in turn exerts a force onto tissue mass 10. Implantation assembly 56 comprises force-distributing device 28, which is mounted on the leading surface of implantation assembly 56, and stopping surface 62, which constitutes the trailing surface of implantation assembly 56. Force-distributing device 28 and stopping surface 62 are separated by spacer 60, which essentially controls the depth of implantation of force-distributing device 28 in tissue mass 10. As shown in FIG. 17*b*, the implantation process proceeds until stopping surface 62 encounters the surface of tissue mass 10.

Figure 18A:
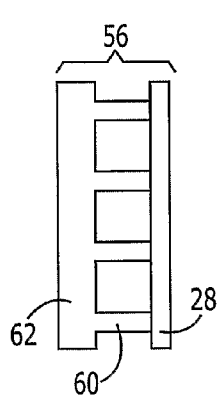
FIGS. 18a-d are section views showing various configurations of the implantation assembly.

FIG. 18*a* shows a detailed cross-section of implantation assembly 56 wherein force-distributing device 28 is attached to the leading surfaces of spacer 60. Force-distributing device 28 may be attached using any appropriate biocompatible glue, such as cyanoacrylate or medical-grade silicone adhesive, or it may be press-fit into features on the surface of spacer 60 that hold force-distributing device 28 in place during implantation. Alternatively, force-distributing device 28 may be heat-staked or laser-welded onto spacer 60, either by melting portions of force-distributing device 28, spacer 60 or both.

Figure 18B:
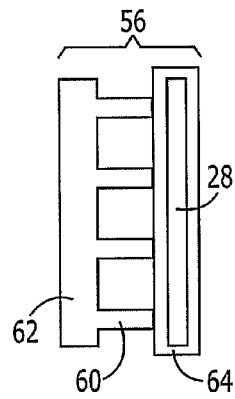
Figure 18C:
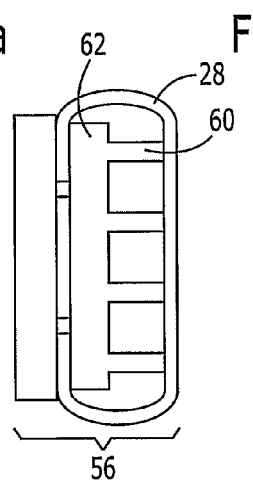
Figure 18D:
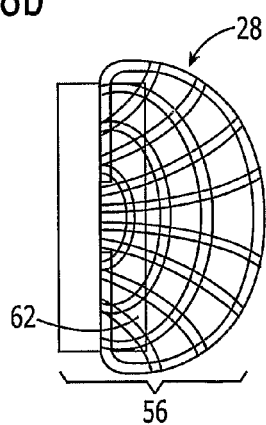

FIG. 18*b* shows an alternative approach to the attachment of force-distributing device 28 to implantation assembly 56 wherein force-distributing device 28 is encased in a degradable material 64. By way of example, force-distributing device 28 may be insert-molded into a molded part comprising the encasement for force-distributing device 28 as well as spacer 60 and stopping surface 62. FIG. 18*c* shows another approach to the attachment of force-distributing device 28 to stopping surface 62 wherein force-distributing device 28 wraps around the edge of implantation assembly 56 and is trapped or glued or otherwise bonded along the side or trailing surface of implantation assembly 56. The advantage of this approach is that no gluing or attachment features are incorporated onto the leading surface of implantation assembly 56, thereby eliminating any issues of biocompatibility of gluing materials and/or unwanted increases in the surface area of the leading surface. FIG. 18*d* shows yet another configuration for attachment of force-distributing device 28 to implantation assembly 56, wherein force-distributing device 28 is formed as a structure which does not require a spacer element. Instead, force-distributing device 28 is attached directly to, or incorporated as part of, stopping surface 62. In the specific embodiment shown in the figure, force-distributing device 28 is depicted as being a mesh that is formed into a pillow shape and attached to stopping surface 62. A disadvantage of this approach is that the material chosen for force-distributing device 28 must be strong enough to exert the desired forces against tissue mass 10 without buckling. This strength will tend to make force-distributing device 28 less supple and therefore more apt to erode through tissue mass 10 after implantation, especially in a mobile tissue mass such as the stomach wall. Another disadvantage of this approach is that after the implantation process is complete, a portion of force-distributing device 28 may extend outside of tissue mass 10. A refinement of the design to eliminate this disadvantage is to form at least the sides of the pillowed force-distributing device 28 out of a degradable material.

Figure 20:
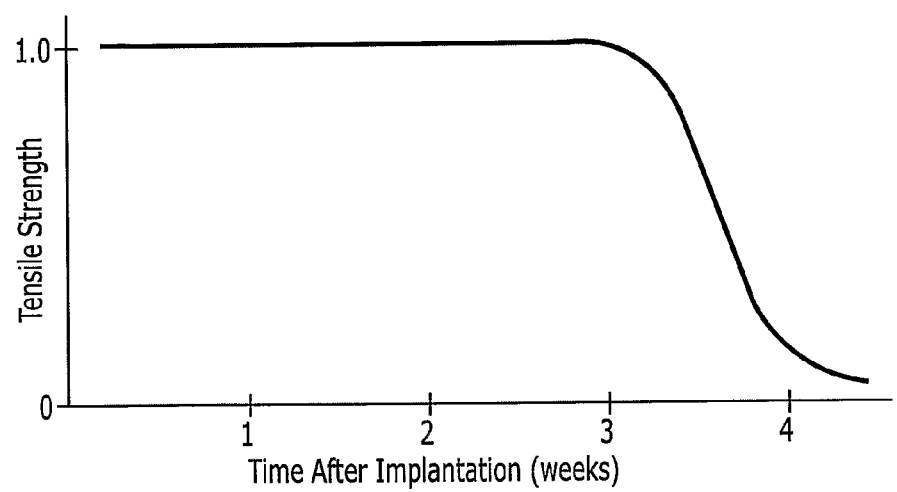
FIG. 20 is a graph showing tensile strength versus time after implantation for a biodegradable material.

The degradable material chosen for the degradable parts of the anchoring system are preferably ones that lose their strength after a predictable amount of time in the target environment. By way of example only, FIG. 20 is a qualitative graph showing tensile strength versus time after implantation for a degradable material. As a further example but not by way of limitation, specific examples of biodegradable polymers are described in "An Overview of Biodegradable Polymers in Biomedical Application," National Research Laboratory, KIST, Korea, September, 2002, and "Lactel Biodegradable Polymers," Absorbable Polymers International, Pelham, Ala., USA, November, 2003. In the case where the anchoring system is intended for use in the GI tract, the materials may be chosen to be similar to those used to encase certain pharmaceutical agents, which are familiar to those skilled in the art, and which are formulated to break down at a predictable rate in the presence of an acid environment into non-toxic components.

Figure 21:
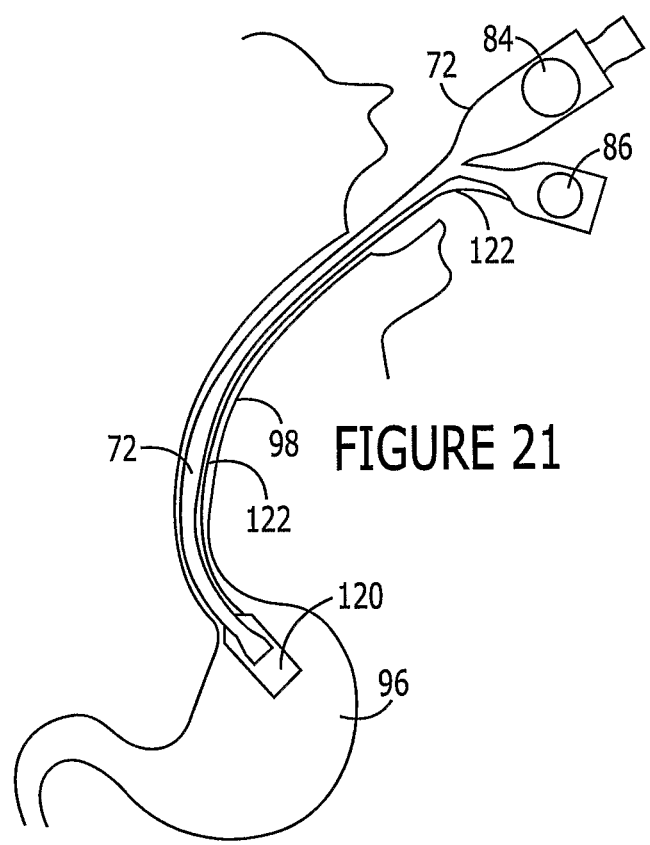
FIG. 21 is a section view of an endoscopic delivery system being passed through the esophagus of a patient into the stomach.

FIG. 21 depicts an endoscopic delivery system for delivering anchoring systems to internal regions of the body. Endoscope 72 is shown passing through esophagus 98 into stomach 96. Endoscope controls 84 remain outside the patient. The anchoring systems are preferably delivered by use of an accessory that attaches to a standard endoscope. As shown in the figure, endoscope 72 may have an endoscopic tip attachment 120 that is controlled by auxiliary controls 86. Auxiliary controls 86 remain outside the patient, and are preferably linked to endoscopic tip attachment 120 by linkage elements which may extend through the working channel (see FIG. 22) of endoscope 72 or through an auxiliary control conduit 122 which may attach to the outside of endoscope 72.

Figure 22:
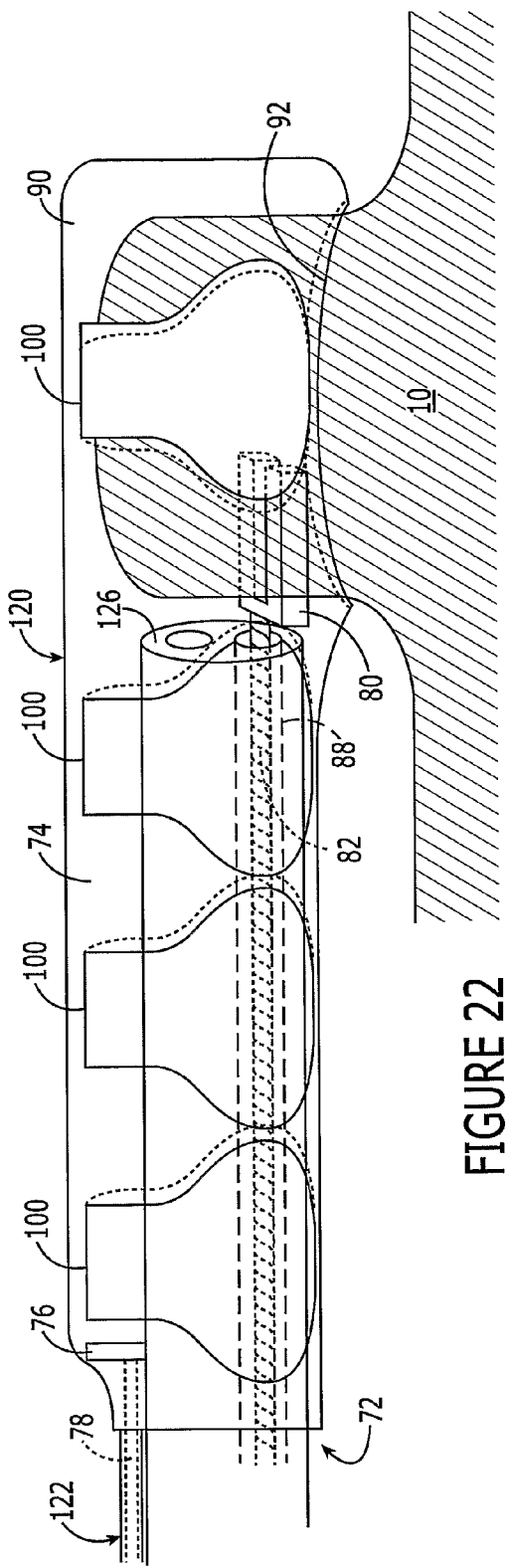
FIG. 22 is a perspective view in partial phantom with certain cutaway views of an endoscopic delivery system for delivering multiple anchoring systems to target tissue masses.

FIG. 22 depicts an example of an endoscopic tip attachment 120 shown attached to the distal tip section of endoscope 72. Attachment 120 has a payload section 74, which holds one or more anchors 100 (e.g., implantation assemblies described previously), and a cavity section 90, which has opening 92. When suction is applied to cavity 90, tissue from a target tissue mass 10 may be sucked into the cavity. The size of opening 92 is related to the amount and thickness of tissue that may be sucked into the cavity, and also to the level of suction applied to the cavity. By way of example only and not by way of limitation, the length of opening 92 may be in the range of 5-40 mm, and the width of opening 92 may be in the range of 5-25 mm. The source of the suction applied to cavity 90 may be through suction/working channel 88, which is available on most standard endoscopes, or it may be applied through an external conduit that may or may not be related to conduit 122. It will be appreciated that if channel 88 is used for the passage of one or more linkage elements, the ability of channel 88 to pass substantial suction may be compromised, in which case an external suction conduit would be preferred. It will be appreciated that tissue may be drawn into cavity 90 by mechanical means instead of, or in addition to, the use of suction. Such means may include tissue grasping forceps, hooks, barbs, claws, pawls, rotating elements or the like.

Once adequate tissue is sucked into cavity 90, anchor 100 may be deployed onto the tissue by activating a deployment mechanism such as that shown in the figure, wherein anchor 100 is held open by hold-off spacer 80. When deployment trigger 82 is activated (by means of auxiliary controls 86), hold-off spacer 80 slips out from under the bottom edges of anchor 100, thereby releasing the spring force of anchor 100 and allowing it to pinch the sucked-in tissue mass. To release the tissue with the anchor attached, the suction source is turned off and the endoscope tip and tip attachment 120 may be moved away from tissue mass 10.

In the case where more than one anchor 100 is carried in payload section 74, the next anchor in the payload is advanced by activating advancing trigger 78, which pushes advancing device 76 thereby moving the next anchor into position in cavity 90. It is assumed that hold-off spacer 80 will be spring-returned to its hold-off position before the next anchor is advanced into cavity 90. Details of such spring-return mechanisms are familiar to those skilled in the art.

Flexible endoscopes used in the GI tract typically have a steering section adjacent to their distal tip that allows the tip to bend in response to inputs from the endoscope controls. The steering function is important in order to enable the endoscope tip to be maneuvered to target tissue locations within the body. The steering section typically may be in the range of 25-100 mm long. In order to maintain steerability, tip attachment 120, and in particular payload section 74, are preferably designed from flexible materials, or designed to have flexible interconnections between short rigid sections.

Another important consideration is the preservation of visualization of endoscope 72, so that the operator may be able to accurately guide the endoscope tip and tip attachment to target tissue locations. Illumination and visualization means are typically disposed on the distal face 126 of the endoscope, and are generally forward-viewing. To minimize impairment of this visualization capability, at least the distal face of tip assembly 120 is made from an optically clear material, such as glass, acrylic, polycarbonate or the like.

Preferably, the entire cavity 90 is made from an optically clear material to enable at least some measure of peripheral visualization.

It will be appreciated that the system depicted in FIG. 22 may be further refined to incorporate a mechanism to apply tissue-pinching clamps 118, such as the one shown in FIG. 34f, to the sucked-in tissue mass. Clamps 118 may be applied to the sucked-in tissue mass by activating a clamp-deploying mechanism (not shown) triggered by a clamp-deployment trigger (also not shown), which may be triggered by auxiliary controls 86 (FIG. 21).

FIG. 24 shows the anchoring system in use for tethering a foreign body 94 to tissue mass 10 by means of passing a securement device 12 through force-distributing device 28 and linking securement device 12 to foreign body 94. At least one end of securement device 12 may be secured by means of a knot or cinching device 104.

FIGS. 25a-b show multiple tissue masses 10 being approximated by use of multiple force-distributing devices 28 embedded in each tissue mass 10 and pulled together by a securement device 12 which has been passed through each mass and through each force-distributing device 28. In FIG. 25b, securement device 12 is tightened and the ends are shown secured by means of a knot or cinching device 104.

FIG. 26 is a perspective view showing the use of multiple anchoring systems in the stomach 96 to create a gastric restriction for treatment of obesity. In the figure, a row of anchors have been placed along the anterior and posterior walls of the stomach, in a line extending from the cardia region 102 along at least a portion of the lesser curvature 132. After placement of the anchors, adequate time is allowed for implantation and/or healing of the anchors into the target layers of the stomach wall. By way of example and not limitation, the target layers may be the submucosa or one of several muscle layers, and the implantation and/or healing time may be between about three days and three months. Once the anchors are fully implanted and the degradable parts have been passed, a securement device such as a thread or suture may be used to lace up the anchors along the seam. This may be done in pairs, whereby, anchors opposite each other on the anterior and posterior walls are brought together, or it may be done by lacing all the anchors together in a fashion similar to lacing a shoe or cinching a laundry bag. The goal of the technique is to create a gastric partition 152 (depicted as a dotted line in FIG. 26), whereby food entering the stomach from esophagus 98 quickly fills the partitioned compartment near cardia 102, giving the patient a feeling of fullness, and then slowly empties into the main portion of the stomach through the narrow channel formed by the rest of the partition that parallels lesser curvature 132.

Another application of the technology disclosed herein is for treatment of gastroesophageal reflux disease (GERD), whereby contents of the stomach reflux into the esophagus. A common cause of GERD is a weakening and enlargement of the lower esophageal sphincter (LES). By placing an array of anchors around the periphery of the LES, which may be in the cardia region of the stomach, and then cinching the anchors together with a securement device, the LES can be effectively tightened, thereby reducing the incidence of reflux episodes. FIGS. 27a-b show the placement of multiple anchors 100 in the cardia region 102 of stomach 96. Securement device 12 is laced through anchors 100, tightened, and then secured with a knot or cinching device 104. The result is a tightening of LES 106, as shown in FIG. 27b, and therefore a possible reduction in episodes of reflux of contents from stomach 96 into esophagus 98.

FIG. 28a shows a variant of the technique described above. Instead of placing anchors around the cardia region of the stomach, anchors are placed is esophagus 98 in the vicinity of LES 106. Securement device 12 is cinched and secured with a knot or cinching device 104, pulling anchors 100 together as shown in FIG. 28b, thereby effectively cinching LES 106 and reducing reflux episodes.

FIGS. 29a-b show yet another application of the technology of the present invention in the GI tract. In FIG. 29a, anchors 100 are shown placed radially in the vicinity of pylorus 108. Securement device 12 is laced through anchors 100 and tightened and secured with a knot or cinching device 104, as shown in FIG. 29b. The purpose of this procedure is to tighten the pylorus and thereby reduce the flow of gastric contents from stomach 96 into duodenum 136, which may extend the feeling of fullness and therefore serve as a treatment for obesity.

FIG. 30 shows still another application of the present technology for application within the GI tract. An array of anchors 100 is disposed radially in the vicinity of pylorus 108, and securement devices 12 are linked between anchors 100 and points of attachment on sleeve 110, which extends at least into duodenum 136. By way of example, sleeve 110 may be a tubular absorption barrier that reduces contact between food passing from stomach 96 and the walls of duodenum 136, where significant fat absorption takes place. Thus, the technique described may serve as an effective treatment for obesity.

FIG. 31 shows another application of the technology disclosed herein for use in the GI tract. Anchors 100 are placed in esophagus 98, for example in the region of LES 106. Valve or flow limiting device 112 is attached to anchors 100 by an array of securement devices 12. Valve or flow limiting device 112 may be a one-way valve, thereby serving to prevent the reflux of contents within stomach 96 into esophagus 98 and providing a treatment for GERD. Alternatively, or in addition to this function, device 112 may restrict the flow of food from esophagus 98 into stomach 96, thereby discouraging overeating and thus providing a treatment for obesity. Such restriction may be accomplished by limiting the size of the opening in device 112 or by selecting the material properties and mechanical design of device 112 so as to make passage of food more difficult.

FIG. 32 shows a particular technique for implanting anchors into the wall of a tubular organ such as the esophagus. Such technique may be used, for example, to place anchors around the LES for the purpose of treating GERD or obesity in ways depicted in FIGS. 28 and 31. In FIG. 32, stent 114 is an expandable tubular device that may be fabricated using many varied techniques familiar to those skilled in the art. By way of example and not limitation, stent 114 may be a self-expanding type made from a material such as nitinol, or it may be of the type which requires an inner expanding member such as a balloon to deploy stent 114 to its expanded state. In any case, the purpose of stent 114 is to exert an outward force against an array of implantation assemblies 56 which are radially deployed between the stent and the wall of the tubular organ. Once implantation assemblies 56 are implanted, stent 114 may be removed or it may be made at least partially from a degradable material that degrades after the implantation process is complete.

FIG. 33a shows an endoscopic device for implanting anchoring systems directly into target tissue masses by use of the techniques described in FIGS. 4a-b and FIGS. 6a-d. The device shown is similar to that described in FIG. 22. Cavity 90 has opening 92 adapted to receive a portion of tissue mass 10. Tissue mass 10 may be drawn into opening 92 by mechanical means (as discussed previously for the embodiment of FIG. 22), or by the application of suction to cavity 90, which may be applied through suction/working channel 88. Once tissue is drawn into cavity 90, cutting and insertion device 138 is triggered by activation of deployment trigger 82 to cut into tissue mass 10. It will be appreciated that due to the mechanical properties of certain types of tissue, the movement of device 138 into tissue mass 10 without exerting significant crushing force onto tissue mass 10 may be difficult. To make such movement easier, device 138 and/or trigger 82 may have a spring-loaded mechanism that rapidly propels device 138 into tissue mass 10. This technique is familiar to those skilled in the art of designing spring-loaded biopsy devices. Alternatively, cutting efficacy of device 138 may be enhanced by having the blade portion of device 138 vibrate and/or by incorporating a reciprocating secondary blade element. Prior to cutting into tissue mass 10, a force-distributing device 28 is loaded onto the side of device 138. This is better depicted in the top view of device 138 shown in FIG. 33b. After device 138 has penetrated into tissue mass 10, device 138 is retracted and force-distributing device 28 is left behind inside tissue mass 10. To ensure that force-distributing device 28 stays within tissue mass 10 and does not pull out when device 138 is retracted, force-distributing device 28 may have a physical feature such as barb 140 shown in FIG. 33b. Barb 140 is preferably made from a degradable material so that it does not cause persistent tissue irritation or erosion after implantation. Referring back to FIG. 33a, after force-distributing device 28 is inserted into tissue mass 10 and device 138 is retracted, tissue mass 10 may be released, and another target tissue mass may then be drawn into cavity 90. Optional payload 74 may contain one or more additional force-distributing devices 28 which can be automatically loaded onto device 138 by activating advancing trigger 78 which pushes on advancing device 76, which in turn moves force-distributing device 28 along payload 74. To load force-distributing device 28 onto device 138, the distal end of payload 74 may have an angled rail 142 which may guide the distal-most force-distributing device 28 onto device 138. It will be appreciated that more elegant mechanisms for sequentially moving force-distributing devices 28 onto device 138 may be crafted by those skilled in the art. It will also be appreciated that the handling and insertion of force-distributing device 28 may be made easier if it is encased at least partially by a more rigid material, which is preferably degradable (see FIG. 18b). FIG. 33c shows an alternative design for device 138, wherein the shape of device 138 is tapered to ease the insertion of the device into the tissue and to facilitate releasing force-distributing device 28 into the tissue when device 138 is retracted.

FIGS. 34a and 34b show prior art securement techniques, while FIGS. 34c-g show various advantages of the present invention over the prior art. In FIG. 34a, tissue mass 10 is shown with adjacent structure 26. FIG. 34b shows a conventional securement device 12, such as a curved suture, passing through tissue mass 10. Due to the force required to penetrate tissue 10, securement device 12 pushes tissue mass 10 outward, in this case into adjacent structure 26. Such a scenario puts adjacent structure 26 at risk of being penetrated or at least nicked by securement device 12, and at further risk of becoming secured to tissue mass 10. In the case where tissue mass 10 is the stomach wall and adjacent structure 26 is a segment of bowel, any unwanted perforation or securement could lead to a serious complication. In FIG. 34c, tissue mass 10 is shown being drawn away from adjacent structure 26 in response to force 14, which may be exerted by the application of suction, such as that shown in FIGS. 22 and 33a, or it may be exerted mechanically by a grasping device such as that shown in FIGS. 15a and 15b. FIGS. 34d and 34e show the result of the various implantation processes, whether accomplished by clamping and erosion or by cutting and direct implantation. As shown, the implantation process is done in such a way as to keep adjacent structure 26 away from harm. FIG. 34f shows a specific embodiment of the tissue tuck formation techniques described in FIGS. 13-15, wherein tissue clamp 118 is shown installed across the base of the tissue tuck. FIG. 34g demonstrates a potential benefit of the tissue tuck techniques described, wherein the outside wall of tissue mass 10 which is pressed together inside the tuck may grow together to form a zone of outer wall knitting 134. This may be particularly useful in cases such as gastric partitioning, where a flap of healed tissue is formed containing at least one force-distributing device 28 and possibly a linkage element 58 to which additional securement devices may be attached.

A further refinement of the methods and devices disclosed herein provides for the addition of tissue-affecting substances on or adjacent to the leading or trailing surfaces of the implantation assembly. Such substances may be tissue-dissolving agents, tissue irritants or other substances which facilitate tissue erosion near the leading edge, regrowth of tissue near the trailing edge, and/or fibrotic scarification of tissue around the force-distributing device during or after the implantation process. Additionally, at least a portion of the implantation assembly may be electrically active so as to promote the erosion and/or regrowth and/or fibrotic scarification of tissue during or after implantation of the force-distributing device. Further, at least a portion of the implantation assembly may be activated during or after implantation to induce tissue irritation or scarification by means of thermal injury (either hot or cold). For example, if at least a portion of the force-distributing device is electrically conductive, an electrical current may pass through the force-distributing device and cause a heating effect at the interface between the force-distributing device and the surrounding tissue.

FIG. 35a shows an anchoring system similar to those embodiments described in FIGS. 14 and 15, with the additional feature of an electrical current generator incorporated into the assembly. The publication entitled "Microcurrent Electro-Physiology Research Abstracts: 1985-1999" (EastWestMed.com) summarizes a large body of research suggesting that the rate of tissue growth and necrosis can be influenced by small electrical currents. It is suggested that the direction of current flow may cause differential effects at the anode and cathode. For this reason, it may be desirable to periodically switch the direction of current flow between the anode and cathode to cancel out such differential effects. Alternatively, it may be desirable to take advantage of such effects. For example, during the initial implantation process, it may be desirable to accelerate the erosion process, while after the implantation assembly has moved into the tissue, it may be desirable to accelerate the tissue growth process. It may also be advantageous to produce a pulsed current or voltage instead of a steady direct current. In FIG. 35a, current generator 150 is shown being integrated with, or attached to, force-producing element 44. Many other configurations will be apparent to those familiar with the art. In all cases, a current flow path must be defined from one region to another. For dual anchoring systems such as the one shown in the figure, it may be convenient for one implantation assembly 56 to function as one electrode, such as the anode, and the other implantation assembly 56 to function as the cathode. Alternatively, current could be configured to flow locally through one or more implantation assemblies, or from one or more implantation assemblies to a separate electrode. FIG. 35b shows a block diagram of the simplest embodiment of electrical current generator 150 shown in FIG. 35*a*. Battery 146 is connected to current source 148, which may be an integrated circuit such as an LM334. The negative output of the battery is connected to the negative output of current generator 150, and the output of current source 148 is connected to the positive output of the battery. It will be appreciated that additional modifications to produce switching functions, pulse functions, high frequency stimulation, certain waveforms and the like are well within the capabilities of those skilled in the art.

Although certain embodiments and examples have been described herein, it will be understood by those skilled in the art that many aspects of the methods and devices shown and described in the present disclosure may be combined differently and/or modified to form still further embodiments. Additionally, it will be recognized that the methods described herein may be practiced using any device suitable for performing the recited steps. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

What is claimed is:

1. A soft tissue anchoring system for linking a first tissue region to a second tissue region or to an object, said system comprising:
   a force-distributing device including a first substantially planar surface area configured to be placed adjacent the first tissue region and to erode through the first tissue region to a target location via a pushing force applied toward the first tissue region, the force-distributing device configured when deployed to the target location to distribute a pulling force away from the first tissue region at the first surface area;
   a stopping surface configured to limit the erosion depth of the force-distributing device to about the target location; and
   a plurality of spacers coupling the stopping surface to the force-distributing device at a plurality of locations to form a spaced relationship between the stopping surface and the force-distributing device at at least one location.

2. The system of claim 1, further including a force-producing element coupled to the stopping surface, the force-producing element configured to create a pushing force toward the first tissue region.

3. The system of claim 2, wherein the first tissue region is adjacent to a hollow anatomical structure, the second tissue region is adjacent to the hollow anatomical structure, or the object is located within the hollow anatomical structure, and the force-distributing device is configured to be placed completely within the hollow anatomical structure, and the first surface area is adjacent the first tissue region.

4. The system of claim 2, wherein the force-distributing device first surface area forms a substantially mesh-like structure configured to accommodate tissue erosion and tissue ingrowth and the first surface area is cofigured to remain substantially constant as the first surface area erodes through the first tissue region.

5. The system of claim 4, wherein at least a portion of the force-distributing device first surface area includes a material whose tensile strength lowers as the force-distributing device first surface area erodes into the first tissue region.

6. The system of claim 2, wherein the force-producing element is configured to be placed completely within the hollow anatomical structure and coupled to the stopping surface.

7. The system of claim 2, wherein the implantable force-producing element is configured to produce an initial, first pushing force great enough to enable the force-distributing device to erode through a portion of the first tissue region and a subsequent, second force not great enough to enable the force-distributing device to continue eroding through a portion of first tissue region.

8. The system of claim 7, wherein the force-producing element is configured to transition from the first force to the second force as a function of time.

9. The system of claim 2, further including an implantable linkage element configured to link the deployed force-distributing device to one of the second tissue region and the object, and wherein the force-distributing device is configured when deployed to the target location to distribute a pulling force applied by the linkage element away from the first tissue region over a portion of the first surface area.

10. The system of claim 9, wherein the force-producing element is configured to create resistance approximately opposite the direction of force applied by the linkage element.

11. The system of claim 1, wherein the force-distributing device includes a plurality of members coupled at the first surface area.

12. The system of claim 11, wherein the force-distributing device plurality of members coupled at the first surface area form a substantially mesh-like structure configured to accommodate tissue erosion and tissue ingrowth, and the first surface area is configured to remain substantially constant as the first surface area erodes through the first tissue region.

13. The system of claim 1, wherein the spacers have a length about equal to the pre-determined depth to the target location.

* * * * *